United States Patent
Chin et al.

(10) Patent No.: US 11,123,052 B2
(45) Date of Patent: *Sep. 21, 2021

(54) TEMPORARY ANASTOMOTIC SEAL AND METHOD

(71) Applicant: MAQUET Cardiovascular LLC, Mahwah, NJ (US)

(72) Inventors: Albert K. Chin, Palo Alto, CA (US); Dwight Morejohn, Davis, CA (US); Charles S. Taylor, San Francisco, CA (US); Steven B. Choi, Mountain View, CA (US); Eugene Reis, San Jose, CA (US); John W. Davis, Mountain View, CA (US); Edwarda Pineda, Mountain View, CA (US); Kushal P. Vepa, Cupertino, CA (US)

(73) Assignee: MAQUET CARDIOVASCULAR LLC, Mahwah, NJ (US)

( * ) Notice: Subject to any disclaimer, the term of this patent is extended or adjusted under 35 U.S.C. 154(b) by 188 days.

This patent is subject to a terminal disclaimer.

(21) Appl. No.: 15/139,017

(22) Filed: Apr. 26, 2016

(65) Prior Publication Data

US 2016/0310117 A1 Oct. 27, 2016

Related U.S. Application Data

(63) Continuation of application No. 13/033,549, filed on Feb. 23, 2011, now Pat. No. 9,345,461, which is a
(Continued)

(51) Int. Cl.
*A61B 17/08* (2006.01)
*A61B 17/00* (2006.01)
(Continued)

(52) U.S. Cl.
CPC .... *A61B 17/0057* (2013.01); *A61B 17/12031* (2013.01); *A61B 17/12036* (2013.01);
(Continued)

(58) Field of Classification Search
CPC .......... A61B 17/0057; A61B 17/12031; A61B 17/12036; A61B 17/12045;
(Continued)

(56) References Cited

U.S. PATENT DOCUMENTS

| 1,052,374 A | 2/1913 | Parr |
| 1,151,300 A | 8/1915 | Soresi |

(Continued)

FOREIGN PATENT DOCUMENTS

| AU | 270419 | 5/1965 |
| DE | 1160573 | 5/1965 |

(Continued)

OTHER PUBLICATIONS

Mahieu, F.M., Alexandre, B .. Bettedorf, P., and Muylder, Ch.DE, "Use of the Brock Punch for Confection of a Shunt Between Ventricles, A Ventricle and Pulmonary Artery or a Ventricle and the Aorta Without Cardio-Pulmonary By-Pass (CPBI)." Acta Chirurqica Belqica. Beloian Suroical Society. Mar. 1975, No. 2, DD. 160-164.
(Continued)

*Primary Examiner* — Jing Rui Ou
(74) *Attorney, Agent, or Firm* — Wesley Scott Ashton

(57) ABSTRACT

Forming a proximal anastomosis on an aortic wall includes method and instrumentation and apparatus for forming an aortic puncture and inserting into the vessel through the puncture a fluid-impervious sealing element with a protruding retainer. An anastomosis of a graft vessel over the puncture is partially completed with the retainer of the sealing element protruding through the partial anastomosis.
(Continued)

The retainer facilitates removal of the sealing element from the partial anastomosis prior to completion of the procedure.

16 Claims, 27 Drawing Sheets

Related U.S. Application Data continuation of application No. 10/123,470, filed on Apr. 15, 2002, now Pat. No. 7,947,062, which is a continuation-in-part of application No. 10/033,614, filed on Dec. 26, 2001, now Pat. No. 6,814,743.

(51) Int. Cl.
*A61B 17/12* (2006.01)
*A61B 17/3205* (2006.01)
*A61B 17/11* (2006.01)

(52) U.S. Cl.
CPC .. *A61B 17/12045* (2013.01); *A61B 17/32053* (2013.01); *A61B 17/1204* (2013.01); *A61B 17/12022* (2013.01); *A61B 17/12027* (2013.01); *A61B 2017/0061* (2013.01); *A61B 2017/00362* (2013.01); *A61B 2017/00575* (2013.01); *A61B 2017/00632* (2013.01); *A61B 2017/00637* (2013.01); *A61B 2017/00641* (2013.01); *A61B 2017/00659* (2013.01); *A61B 2017/1107* (2013.01)

(58) Field of Classification Search
CPC ........ A61B 17/32053; A61B 17/12022; A61B 17/12027; A61B 2017/00659; A61B 17/1204; A61B 2017/00362; A61B 2017/00575; A61B 2017/0061; A61B 2017/00632; A61B 2017/00637; A61B 2017/00641; A61B 2017/1107
See application file for complete search history.

(56) References Cited

U.S. PATENT DOCUMENTS

| | | | |
|---|---|---|---|
| 1,867,624 | A | 7/1932 | Hoffman |
| 2,453,056 | A | 11/1948 | Zack |
| 2,850,007 | A | 9/1958 | Lingley |
| 2,919,692 | A | 1/1960 | Ackermann |
| 3,034,680 | A * | 5/1962 | Steinberg ............ B65D 47/103 220/266 |
| 3,104,666 | A | 9/1963 | Hale et al. |
| 3,253,594 | A | 5/1966 | Matthews |
| 3,254,650 | A | 6/1966 | Collito |
| 3,394,699 | A | 7/1968 | Koett |
| 3,561,429 | A | 2/1971 | Jewett |
| 3,628,524 | A | 12/1971 | Jamshidi |
| 3,683,891 | A | 8/1972 | Eskridge et al. |
| 3,774,615 | A | 11/1973 | Lim et al. |
| 3,776,237 | A | 12/1973 | Hill et al. |
| 3,874,388 | A | 4/1975 | King et al. |
| 3,882,849 | A | 5/1975 | Jamshidi |
| 3,993,078 | A | 11/1976 | Bergentz et al. |
| 4,010,543 | A | 3/1977 | Nusbaum |
| 4,010,737 | A | 3/1977 | Vilaghy et al. |
| 4,018,228 | A | 4/1977 | Goosen |
| 4,122,855 | A | 10/1978 | Tezel |
| 4,216,776 | A | 8/1980 | Downie et al. |
| 4,243,048 | A | 1/1981 | Griffin |
| 4,282,884 | A | 8/1981 | Boebel |
| 4,314,565 | A | 2/1982 | Lee |
| 4,352,358 | A | 10/1982 | Angelchik |
| 4,388,925 | A | 6/1983 | Burns |
| 4,469,109 | A | 9/1984 | Mehl |
| D281,721 | S | 12/1985 | Scanlan |
| 4,607,637 | A | 8/1986 | Berggren et al. |
| 4,624,257 | A | 11/1986 | Berggren et al. |
| 4,682,606 | A | 7/1987 | Decaprio |
| 4,699,154 | A | 10/1987 | Lindgren |
| 4,733,671 | A | 3/1988 | Mehl |
| 4,738,261 | A | 4/1988 | Enstrom |
| 4,744,364 | A | 5/1988 | Kensey |
| 4,753,637 | A | 6/1988 | Horneffer |
| 4,721,109 | A | 10/1988 | Healey |
| 4,785,826 | A | 11/1988 | Ward |
| 4,794,928 | A | 1/1989 | Kletschka |
| 4,819,819 | A * | 4/1989 | Robertson, Jr. ...... B65D 47/103 215/230 |
| 4,852,568 | A | 8/1989 | Kensey |
| 4,917,089 | A * | 4/1990 | Sideris ............... A61B 17/0057 128/899 |
| 4,917,090 | A | 4/1990 | Berggren et al. |
| 4,917,091 | A | 4/1990 | Berggren et al. |
| 4,921,478 | A | 5/1990 | Solano et al. |
| 4,931,042 | A | 6/1990 | Holmes et al. |
| 4,961,430 | A | 10/1990 | Sheahom |
| 5,005,585 | A | 4/1991 | Mazza |
| 5,018,530 | A | 5/1991 | Rank et al. |
| 5,036,868 | A | 8/1991 | Berggren et al. |
| 5,108,420 | A | 4/1992 | Marks |
| 5,108,421 | A | 4/1992 | Fowler |
| 5,116,357 | A | 5/1992 | Eberbach et al. |
| 5,122,122 | A | 6/1992 | Allgood |
| 5,129,913 | A | 7/1992 | Ruppert |
| 5,147,374 | A | 9/1992 | Fernandez |
| 5,172,702 | A | 12/1992 | Leigh et al. |
| 5,176,687 | A | 1/1993 | Hasson et al. |
| 5,192,294 | A | 3/1993 | Blake, III |
| 5,192,301 | A | 3/1993 | Kamiya et al. |
| 5,197,971 | A | 3/1993 | Bonutti |
| 5,222,974 | A | 6/1993 | Kensey et al. |
| 5,258,000 | A | 11/1993 | Gianturco |
| 5,273,519 | A | 12/1993 | Koros et al. |
| 5,290,249 | A | 3/1994 | Foster et al. |
| 5,304,193 | A | 4/1994 | Zhadanov |
| 5,312,417 | A | 5/1994 | Wilk |
| 5,312,435 | A | 5/1994 | Nash et al. |
| 5,313,958 | A | 5/1994 | Vauer |
| 5,323,789 | A | 6/1994 | Berggren et al. |
| 5,330,446 | A | 7/1994 | Weldon et al. |
| 5,330,497 | A | 7/1994 | Freitas et al. |
| 5,342,393 | A | 8/1994 | Stack |
| 5,350,399 | A | 9/1994 | Erlebacher et al. |
| 5,358,488 | A | 10/1994 | Suriyapa |
| 5,383,896 | A | 1/1995 | Gershony et al. |
| 5,383,897 | A | 1/1995 | Wholey |
| 5,395,383 | A | 3/1995 | Adams et al. |
| 5,397,331 | A | 3/1995 | Himpens et al. |
| 5,403,338 | A | 4/1995 | Milo |
| 5,413,571 | A | 5/1995 | Katsaros et al. |
| 5,423,330 | A | 6/1995 | Lee |
| 5,454,833 | A | 10/1995 | Boussignac et al. |
| 5,470,320 | A | 11/1995 | Tiefenbrun et al. |
| 5,476,469 | A | 12/1995 | Hathaway et al. |
| 5,478,320 | A | 12/1995 | Trotta |
| 5,488,958 | A | 2/1996 | Topel et al. |
| 5,496,332 | A | 3/1996 | Sierra et al. |
| 5,515,861 | A | 5/1996 | Smith |
| D372,310 | S | 7/1996 | Hartnett |
| 5,531,759 | A * | 7/1996 | Kensey ............... A61B 17/0057 604/15 |
| 5,545,178 | A | 8/1996 | Kensey et al. |
| 5,593,422 | A | 1/1997 | Muijs Van de Moer et al. |
| 5,620,461 | A | 4/1997 | Muijs Van De Moer et al. |
| 5,630,833 | A | 5/1997 | Katsaros et al. |
| 5,634,936 | A | 6/1997 | Linden et al. |
| 5,662,681 | A * | 9/1997 | Nash .................. A61B 17/0057 604/285 |
| 5,676,689 | A * | 10/1997 | Kensey ............... A61B 17/0057 604/168.01 |
| 5,688,286 | A | 11/1997 | Yoon |
| 5,690,674 | A | 11/1997 | Diaz |
| 5,695,504 | A | 12/1997 | Gifford, III et al. |
| 5,700,277 | A | 12/1997 | Nash et al. |
| 5,702,412 | A | 12/1997 | Popov et al. |

(56) References Cited

U.S. PATENT DOCUMENTS

| | | | |
|---|---|---|---|
| 5,746,760 A | 5/1998 | Humphrey, Jr. |
| 5,749,883 A | 5/1998 | Halpern |
| 5,766,220 A | 6/1998 | Moenning |
| 5,772,986 A | 6/1998 | Kross |
| 5,782,860 A | 7/1998 | Epstein et al. |
| 5,788,651 A | 8/1998 | Weilandt |
| 5,797,933 A | 8/1998 | Snow et al. |
| 5,797,953 A * | 8/1998 | Tekulve | A61B 17/12022 606/200 |
| 5,817,113 A | 10/1998 | Gifford, III et al. |
| 5,826,251 A | 10/1998 | Kiendl |
| 5,827,316 A | 10/1998 | Young et al. |
| 5,865,802 A | 2/1999 | Yoon et al. |
| 5,881,943 A | 3/1999 | Heck et al. |
| 5,893,369 A | 4/1999 | LeMole |
| 5,904,697 A | 5/1999 | Gifford, III et al. |
| 5,910,153 A | 6/1999 | Mayenberger |
| 5,944,730 A | 8/1999 | Nobles et al. |
| 5,984,940 A | 11/1999 | Davis et al. |
| 6,007,495 A | 12/1999 | Matula |
| 6,010,517 A | 1/2000 | Baccaro |
| 6,022,367 A | 2/2000 | Sherts |
| 6,036,710 A | 3/2000 | McGarry et al. |
| 6,080,173 A | 6/2000 | Williamson, IV et al. |
| 6,080,175 A | 6/2000 | Hogendijk |
| 6,080,176 A | 6/2000 | Young |
| 6,093,154 A | 7/2000 | Burek et al. |
| 6,110,187 A | 8/2000 | Donlon |
| 6,142,955 A | 11/2000 | Farascioni et al. |
| 6,156,050 A | 12/2000 | Davis et al. |
| 6,168,623 B1 | 1/2001 | Fogarty et al. |
| 6,171,319 B1 | 1/2001 | Nobles et al. |
| 6,171,321 B1 | 1/2001 | Gifford, III et al. |
| 6,171,329 B1 | 1/2001 | Shaw et al. |
| 6,174,322 B1 | 1/2001 | Schneidt |
| 6,176,413 B1 | 1/2001 | Heck et al. |
| 6,180,848 B1 | 1/2001 | Flament et al. |
| 6,183,486 B1 | 2/2001 | Snow et al. |
| 6,214,029 B1 | 4/2001 | Thill et al. |
| 6,248,119 B1 | 6/2001 | Solem |
| 6,273,861 B1 | 8/2001 | Bates et al. |
| 6,280,460 B1 | 8/2001 | Bolduc et al. |
| 6,214,022 B1 | 10/2001 | Taylor et al. |
| 6,371,964 B1 | 4/2002 | Gifford, III et al. |
| 6,371,965 B2 | 4/2002 | Gifford, III et al. |
| 6,375,671 B1 | 4/2002 | Kobayashi et al. |
| 6,387,105 B1 | 5/2002 | Gifford, III et al. |
| 6,395,015 B1 | 5/2002 | Borst et al. |
| 6,409,739 B1 | 6/2002 | Nobles et al. |
| 6,416,527 B1 | 7/2002 | Berg et al. |
| 6,428,555 B1 | 8/2002 | Koster, Jr. |
| 6,443,965 B1 | 9/2002 | Gifford, III et al. |
| 6,451,034 B1 | 9/2002 | Gifford, III et al. |
| 6,464,712 B1 | 10/2002 | Epstein et al. |
| 6,488,636 B2 | 12/2002 | Bryan et al. |
| 6,491,704 B2 | 12/2002 | Gifford, III et al. |
| 6,491,705 B2 | 12/2002 | Gifford, III et al. |
| D472,318 S | 3/2003 | Solem |
| 6,537,300 B2 | 3/2003 | Girton |
| 6,579,225 B2 | 6/2003 | Pregenzer et al. |
| 6,616,684 B1 | 9/2003 | Vidlund et al. |
| 6,652,555 B1 | 11/2003 | VanTassel et al. |
| 6,712,831 B1 | 3/2004 | Kaplan et al. |
| 6,814,743 B2 | 11/2004 | Chin et al. |
| 7,544,203 B2 * | 6/2009 | Chin | A61B 17/0057 606/151 |
| 9,345,461 B2 | 5/2016 | Chin et al. |
| 2001/0000903 A1 | 5/2001 | Heck et al. |
| 2001/0001122 A1 | 5/2001 | Gifford, III et al. |
| 2001/0001825 A1 | 5/2001 | Snow et al. |
| 2001/0004697 A1 | 6/2001 | Blatter et al. |
| 2001/0004698 A1 | 6/2001 | Blatter et al. |
| 2001/0016749 A1 | 8/2001 | Blatter et al. |
| 2001/0021856 A1 | 9/2001 | Bolduc et al. |
| 2001/0023354 A1 | 9/2001 | Blatter et al. |
| 2001/0037129 A1 | 10/2001 | Thill |
| 2001/0047179 A1 | 11/2001 | Gifford, III et al. |
| 2002/0019643 A1 | 2/2002 | Gifford, III et al. |
| 2002/0029007 A1 | 3/2002 | Bryan et al. |
| 2002/0029049 A1 | 3/2002 | Gifford, III et al. |
| 2002/0029050 A1 | 3/2002 | Gifford, III et al. |
| 2002/0038127 A1 | 3/2002 | Blatter et al. |
| 2002/0042623 A1 | 4/2002 | Blatter et al. |
| 2002/0065474 A1 | 5/2002 | Viola |
| 2002/0077537 A1 | 6/2002 | Vargas et al. |
| 2002/0082614 A1 | 6/2002 | Logan et al. |
| 2002/0082626 A1 | 6/2002 | Donohoe et al. |
| 2002/0087175 A1 | 7/2002 | Gifford, III et al. |
| 2002/0111619 A1 | 8/2002 | Keast et al. |
| 2002/0151914 A1 | 10/2002 | Gifford, III et al. |
| 2002/0173809 A1 | 11/2002 | Fleischman et al. |
| 2002/0177865 A1 | 11/2002 | McIntosh |
| 2002/0177885 A1 | 11/2002 | McIntosh |
| 2002/0188317 A1 | 12/2002 | Rousseau |
| 2003/0023251 A1 | 1/2003 | Gifford, III et al. |
| 2003/0065347 A1 | 4/2003 | Gifford, III et al. |
| 2004/0019360 A1 | 1/2004 | Farnsworth et al. |
| 2005/0080439 A1 | 4/2005 | Carson et al. |

FOREIGN PATENT DOCUMENTS

| | | |
|---|---|---|
| DE | 19650204 C2 | 6/1998 |
| EP | 0373927 | 6/1990 |
| EP | 0544485 A1 | 6/1993 |
| EP | 0882429 A1 | 12/1998 |
| EP | 0894475 A1 | 2/1999 |
| EP | 1088519 A1 | 4/2001 |
| SU | 125870 | 5/1960 |
| WO | 9208513 | 5/1992 |
| WO | 9212676 | 8/1992 |
| WO | 9517127 A1 | 6/1995 |
| WO | 9625886 | 8/1996 |
| WO | 9713463 | 4/1997 |
| WO | 9747261 | 12/1997 |
| WO | 9807399 | 2/1998 |
| WO | 9842262 | 10/1998 |
| WO | 9940851 | 8/1999 |
| WO | 9962415 | 12/1999 |
| WO | 199962415 | 12/1999 |
| WO | 0056226 | 9/2000 |
| WO | 200056226 | 9/2000 |
| WO | 0059380 | 10/2000 |
| WO | 200059380 | 10/2000 |
| WO | 0069346 | 11/2000 |
| WO | 0069349 | 11/2000 |
| WO | 200069346 | 11/2000 |
| WO | 200069349 | 11/2000 |
| WO | 0074579 A2 | 12/2000 |
| WO | 200074579 A2 | 12/2000 |
| WO | 02/23224 A2 | 3/2002 |
| WO | 0232293 A2 | 4/2002 |
| WO | 0232323 A2 | 4/2002 |
| WO | 0232324 A2 | 4/2002 |
| WO | 200232293 A2 | 4/2002 |
| WO | 200232323 A2 | 4/2002 |
| WO | 200232324 A2 | 5/2002 |
| WO | 0247532 A2 | 6/2002 |
| WO | 0247561 A1 | 6/2002 |
| WO | 02058568 A1 | 8/2002 |
| WO | 2002058568 A1 | 8/2002 |
| WO | 02074188 A2 | 9/2002 |
| WO | 03030753 A1 | 4/2003 |

OTHER PUBLICATIONS

Murakami, T., Yanagi, H .. Irie. H. Sando, K .. Nakayama, Y., Mondori, E., Tao, M .. Nawa. S., Senoo, Y .. et al., "Experience With Sequential Bypass Grafts Using a Vascular Punch." Journal of the Japanese Association for Thoracic Surgery,. 35/1) , 1987, DD. 20-25.

Notification of International Search Report, PCT/US02/41586, dated Dec. 9, 2003, 6 pages.

(56) References Cited

OTHER PUBLICATIONS

Written Opinion, PCT/US02/41586, dated Jul. 15, 2004 5 pages.
Heijman et al., "Temporary Luminal Arteriotomy Seal: II. Coronary Artery Bypass Grafting on the Beating Heart," Ann. Thorac. Sura., 1998, oo. 471-476, vol. 66.
Hawley's Condensed Chemical Dictionary 22 and 1093 (2001), labeled as Exhibit A2.
The American Heritage Desk Dictionary 300 (1981).
The American Heritage Desk Dictionary, 1981, 67.
Non-Final Office Action issued in U.S. Appl. No. 10/123,470, dated Jan. 11, 2005, 6 pages.
Non-Final Office Action issued in U.S. Appl. No. 10/123,470, dated Jun. 21, 2005, 8 pages.
Final Office Action issued in U.S. Appl. No. 10/123,470, dated Dec. 8, 2005, 6 pages.
Non-Final Office Action issued in U.S. Appl. No. 10/123,470, dated Jun. 23, 2006, 6 pages.
Final Office Action issued in U.S. Appl. No. 10/123,470, dated Jan. 9, 2007, 6 pages.
Non-Final Office Action issued in U.S. Appl. No. 10/123,470, dated Aug. 13, 2007, 5 pages.
Non-Final Office Action issued in U.S. Appl. No. 10/123,470, dated Apr. 10, 2008, 7 pages.
Non-Final Office Action issued in U.S. Appl. No. 10/952,392, dated Jun. 25, 2008, 12 pages.
Final Office Action issued in U.S. Appl. No. 10/123,470, dated Jul. 18, 2008, 7 pages.
Non-Final Office Action issued in U.S. Appl. No. 10/123,470, dated Dec. 3, 2008, 6 pages.
Final Office Action issued in U.S. Appl. No. 10/952,392, dated Dec. 24, 2008, 8 pages.
Final Office Action issued in U.S. Appl. No. 10/123,470, dated Mar. 6, 2009, 6 pages.
Non-Final Office Action issued in U.S. Appl. No. 10/123,470, dated Sep. 23, 2009, 6 pages.
Final Office Action issued in U.S. Appl. No. 10/123,470, dated Apr. 27, 2010, 8 pages.
Non-Final Office Action issued in U.S. Appl. No. 13/033,549, dated May 1, 2012, 13 pages.
Final Office Action issued in U.S. Appl. No. 13/033,549, dated Feb. 6, 2013, 15 pages.
Non-Final Office Action issued in U.S. Appl. No. 13/033,549, dated Nov. 8, 2013, 12 pages.
Final Office Action issued in U.S. Appl. No. 13/033,549, dated Aug. 29, 2014, 17 pages.

\* cited by examiner

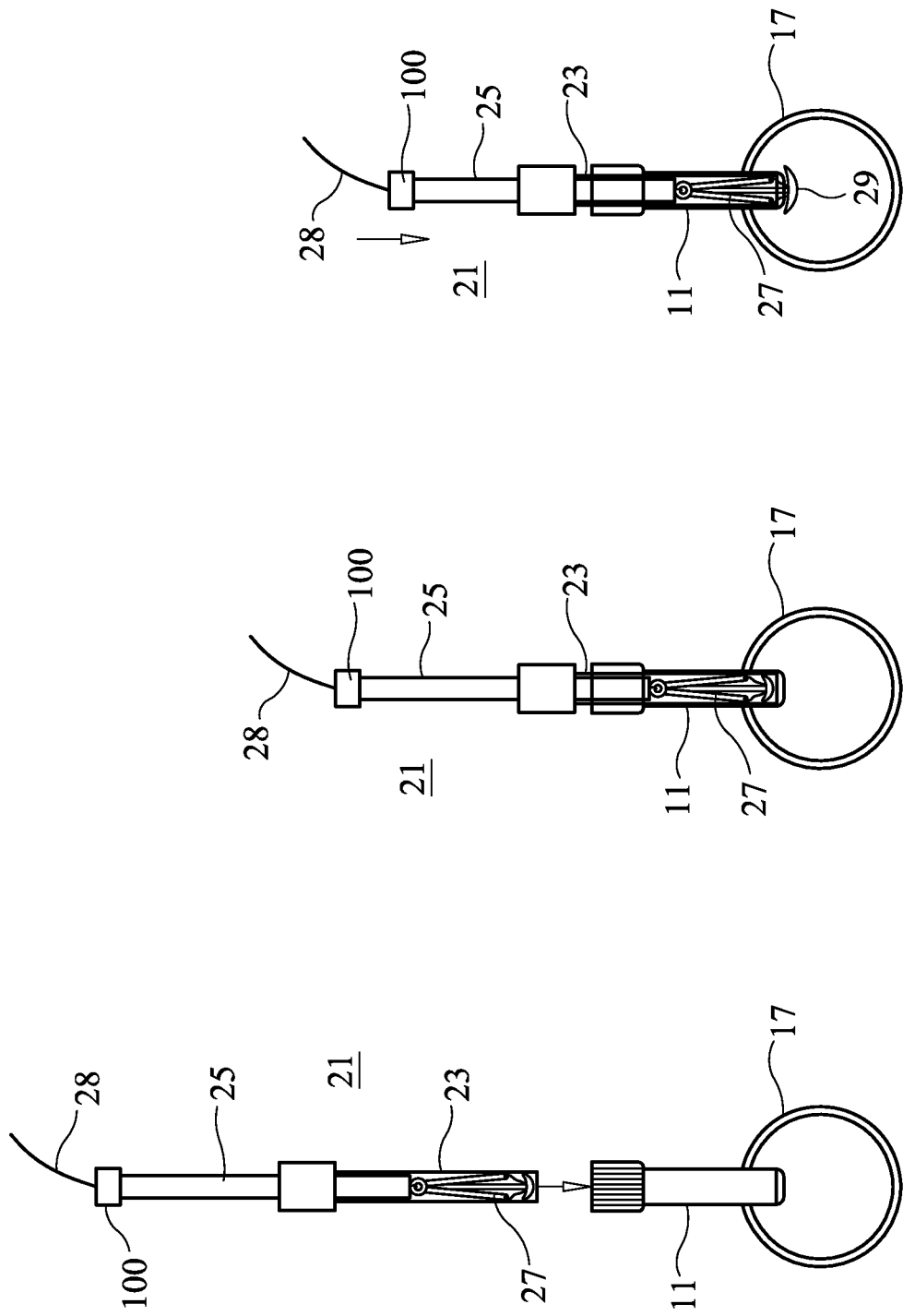

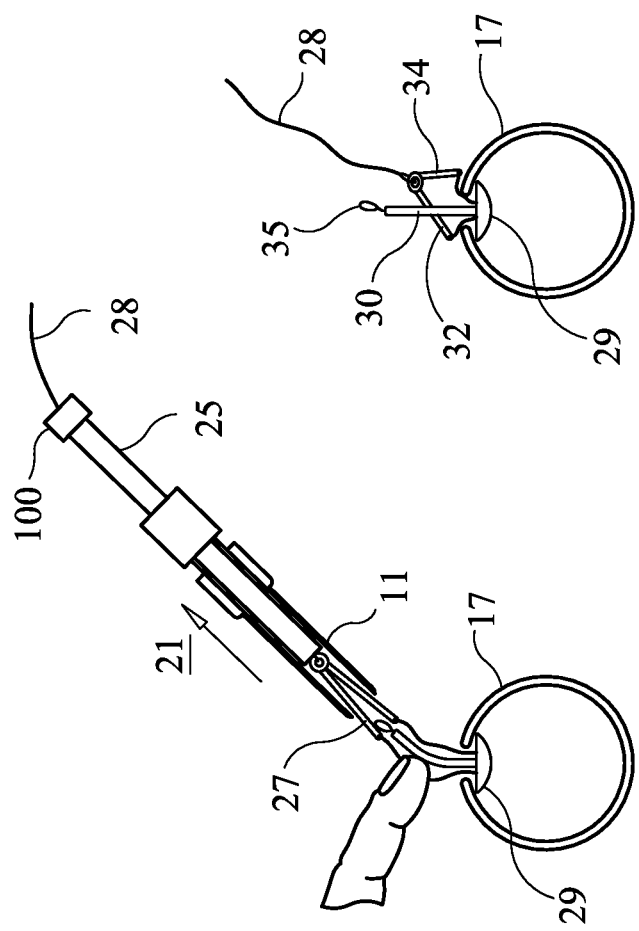

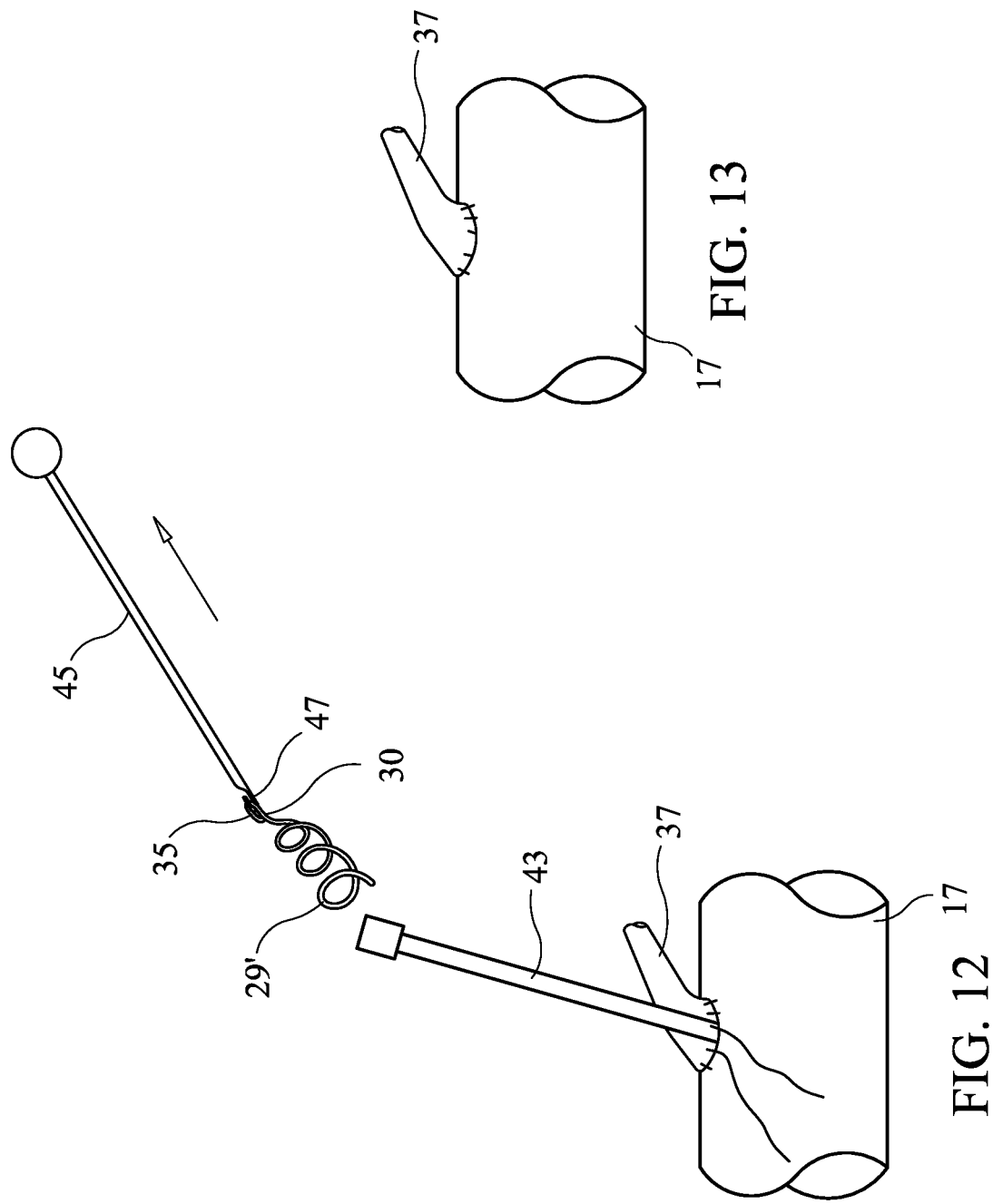

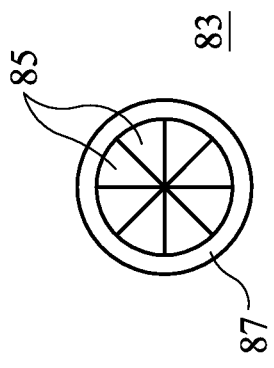
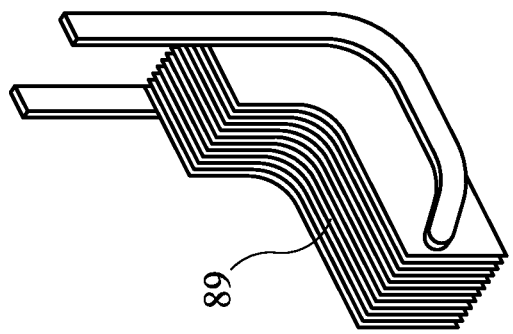
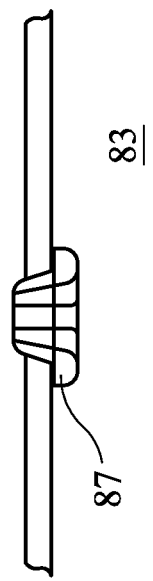
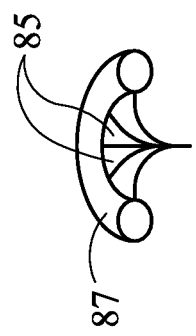
FIG. 23A
FIG. 23B
FIG. 23C
FIG. 24A

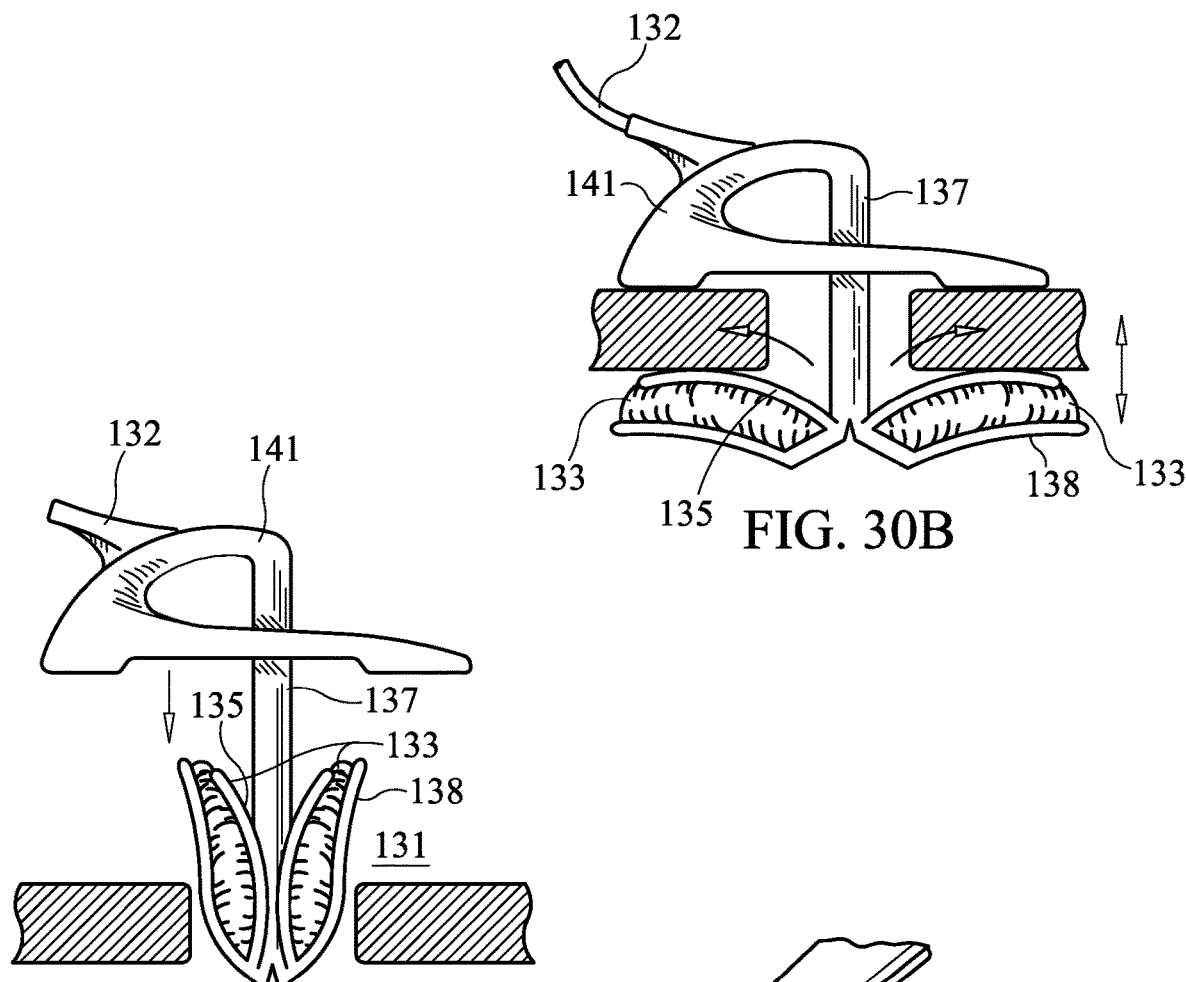
FIG. 30B
FIG. 30A
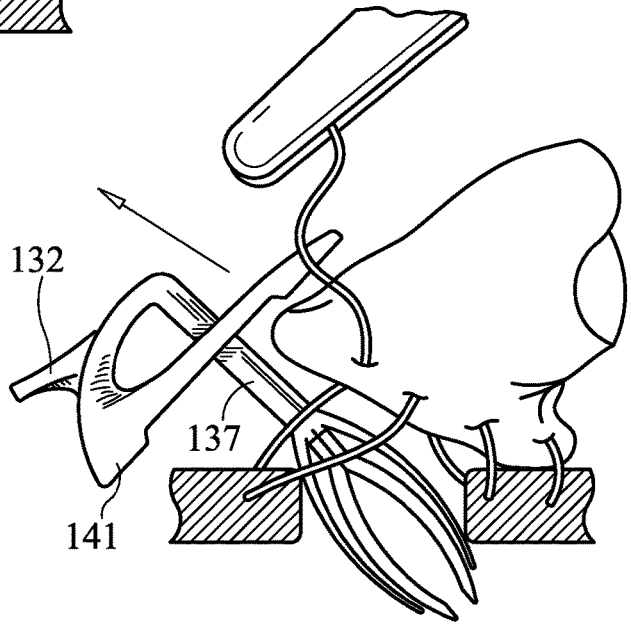
FIG. 30C

TEMPORARY ANASTOMOTIC SEAL AND METHOD

RELATED APPLICATION

This application is a continuation of application Ser. No. 13/033,549, filed on Feb. 23, 2011 (now U.S. Pat. No. 9,345,461), which is a continuation of application Ser. No. 10/123,470, filed on Apr. 15, 2002 (now U.S. Pat. No. 7,947,062), which is a continuation-in-part of application Ser. No. 10/033,614, entitled "Temporary Seal And Method For Facilitating Anastomosis," filed on Dec. 26, 2001 by A. Chin et al. (now U.S. Pat. No. 6,814,743). All of the above mentioned patents and patent applications are incorporated herein by reference in their entirety for all that they disclose.

FIELD OF THE INVENTION

This invention relates to coronary bypass grafting surgery and more particularly to instruments and method to facilitate performing an aortotomy and proximal anastomosis, for example, associated with coronary artery bypass grafting surgery.

BACKGROUND OF THE INVENTION

Contemporary coronary artery bypass grafting surgery is performed on a beating heart to obviate complications commonly associated with prior surgical practices of transitioning a patient onto and off of a heart-lung machine that maintained circulation while the heart was in quiescent condition during construction of a coronary arterial bypass. However, performing an aortotomy and a proximal anastomosis on the aorta that is perfused with blood under pressure contribute to substantial losses of blood in the absence of temporary measures taken to curtail blood flow through the aortic hole. Side-bite and surface-oriented clamping mechanisms have been used to diminish loss of blood during the surgical procedures of punching the aortic hole and anastomosing the graft vessel, but such temporary occlusions damage the endothelium and dislodge emboli that may migrate through the circulatory system. Alternative schemes for performing an aortotomy and limiting loss of blood during the period of anastomosing a bypass graft include introducing a plug or seal at the site of the aortotomy, but such schemes commonly inhibit convenient and rapid completion of the graft anastomosis, and present other complications to be resolved following the grafting procedure.

SUMMARY OF THE INVENTION

In accordance with the method and instrumentation of the present invention, an aorto-coronary bypass graft is performed using an aortic punch and instruments that selectively deliver and position seals of various configurations within the punched aortic hole for retention against the aortic wall. The suture anastomosis is performed with the hemostatic seal in place for removal of the seal prior to completion of the anastomosis.

In accordance with a non-limiting first embodiment of this disclosure, an apparatus is provided for forming a temporary fluid-tight seal on the inner wall of a fluid conduit within a patient's body, wherein the apparatus comprises a fluid-impervious flange having an outer periphery and a stem centrally formed thereon, the flange including a continuous region of diminished shear strength extending from the stem along a continuous path to the periphery for selectively reconfiguring the flange in response to tension applied to the stem to disassemble the flange along the continuous region into a continuous strand. In accordance with a non-limiting second embodiment of this disclosure, the non-limiting first embodiment is modified so that the apparatus includes an elongated hollow sheath having an open distal end, and the sheath is positioned about the stem and about the flange disposed therein in confined configuration near the distal end of the sheath.

In accordance with a non-limiting third embodiment of this disclosure, the non-limiting first embodiment is modified so that the apparatus includes a plunger slidably disposed within the sheath near a proximal end thereof for selectively ejecting the fluid-impervious flange from the distal end of the sheath in response to sliding movement of the plunger within the sheath toward the distal end thereof. In accordance with a non-limiting fourth embodiment of this disclosure, the non-limiting first embodiment is modified so that the apparatus includes a resilient member that extends laterally and includes a pair of mating ends disposed to traverse the periphery of the flange; and a strand of flexible material attached to the mating ends and to one of the stem and flange for supporting the stem and flange intermediate the mating ends of the resilient member; and wherein the sheath is positioned about the flange and about the stem and the resilient member that are confined within the sheath at locations therein proximal the distal end. In accordance with a non-limiting fifth embodiment, the non-limiting fourth embodiment is further modified so that a plunger is disposed within the sheath near a proximal end thereof and includes a lumen therethrough; and a length of line is attached to the resilient member and passes through the lumen in the plunger; wherein the plunger is slidably disposed within the sheath to selectively eject the flange and stem and resilient member and strand from the distal end in response to sliding movement of the plunger within the sheath toward the distal end thereof.

In accordance with a non-limiting sixth embodiment of this disclosure, an apparatus is provided for forming a temporary fluid-tight seal on the inner wall of a fluid conduit within a patient's body, the apparatus comprising a fluid-impervious flange having an outer periphery and a locator thereon disposed to protrude through an aperture in a wall of the fluid conduit for positioning the flange against an inner wall over the aperture; and wherein the flange is selectively reconfigurable for removal from the aperture. In accordance with a non-limiting seventh embodiment, the non-limiting sixth embodiment is modified so that a locator on the flange extends to a conduit outer wall beyond the aperture for providing force on the flange against the inner wall of the conduit.

In accordance with a non-limiting eighth embodiment of this disclosure, the non-limiting sixth embodiment is modified so that the flange includes a plurality of ribs radially disposed about a distal end of the locator, and including a web of flexible material disposed about the plurality of ribs to form the fluid impervious flange for retention against an inner wall of the fluid conduit, and for retrieval therefrom as reconfigured for removal through the aperture. In accordance with a non-limiting ninth embodiment, the non-limiting sixth embodiment is modified so that the flange includes an annular rim having an elevated central region for positioning within and about the aperture under tensile force applied thereto from outside the fluid conduit. In accordance with a non-limiting tenth embodiment, the non-limiting sixth embodiment is modified so that the flange includes a resilient plate for positioning against an inner wall of the fluid conduit at a location covering the aperture and for retrieval therefrom through the aperture and an incomplete segment of an anastomosis to the fluid conduit of a graft vessel in fluid communicating alignment with the aperture.

In accordance with a non-limiting eleventh embodiment of this disclosure, a temporary sealing element is provided for forming a fluid-tight seal on the inner wall of a fluid conduit within a patient's body, the temporary sealing element comprising a fluid impervious flange having an outer stem centrally formed thereon, the flange including a continuous region of diminished shear strength extending from the stem along a continuous path to the periphery for selectively reconfiguring the flange in response to tension applied to the stem to dissemble the flange along the continuous region into a continuous strand. In accordance with a non-limiting twelfth embodiment, the non-limiting eleventh embodiment is modified to include a length of flexible, resilient material integrally forming the stem, and that is helically wound to form successive convolutes from the stem to the periphery, with each convolute adhering to adjacent convolutes along lateral edges thereof to form the continuous region in the substantially fluid impervious flange.

In accordance with a non-limiting thirteenth embodiment of this disclosure, the non-limiting twelve embodiment is modified so that the length of material includes a length of bioinert thermoplastic material forming the stem and the flange and including thermoplastic adhesion between lateral edges of adjacent convolutes of the helically-wound length of material. In accordance with a non-limiting fourteenth embodiment, the non-limiting thirteenth embodiment is modified so that thermoplastic material is polyvinyl chloride.

In accordance with a non-limiting fifteenth embodiment, the non-limiting twelfth embodiment is modified to include an attachment structure at an end of the stem remote from the flange for selective engagement therewith to exert tensile force thereon. In accordance with a non-limiting sixteenth embodiment, the non-limiting twelfth embodiment is modified to include a support structure attached to one of the stem and flange and that includes a resilient member disposed to expand from a confined configuration of smaller lateral dimension than the periphery of the flange to an expanded configuration of larger lateral dimension than the periphery of the flange. In accordance with a non-limiting seventeenth embodiment, the non-limiting sixteenth embodiment is modified so that the resilient member extends laterally and includes a pair of mating ends disposed to traverse the periphery of the flange, and a strand attached to the mating ends and to one of the stem and flange for supporting the stem and flange intermediate the mating ends of the resilient member. In accordance with a non-limiting eighteenth embodiment, the seventeenth embodiment is modified so that the resilient member includes a pair of arms extending to and including the mating ends and that are resiliently biased for outward extension of the mating ends.

In accordance with a non-limiting nineteenth embodiment, the non-limiting twelfth embodiment is modified so that the flange is formed of flexible resilient material and includes a generally circular periphery and the stem integrally formed therewith, and the region of diminished shear strength extends from the stem along a substantially helical path to the periphery.

BRIEF DESCRIPTION OF THE DRAWINGS

FIGS. 4 and 5 are pictorial illustrations of a seal-positioning mechanism for insertion through the hemostatic sheath into the aorta;

FIG. 6 is a pictorial illustration of the hemostatic seal mechanism deployed from the interior end of the hemostatic sheath;

FIG. 7 is a pictorial illustration of the hemostatic seal mechanism manually positioned within the punched aortic hole as the hemostatic sheath and hemostatic seal-positioning mechanism are withdrawn;

FIG. 8 is a pictorial illustration of the hemostatic seal retained in place at the punched aortic hole via an external tensioning mechanism;

FIG. 9 is a pictorial illustration of suture anastomosis performed about the hemostatic seal;

FIG. 12 is a pictorial frontal illustration of the hemostatic seal dissembled through the tubular removal instrument;

FIG. 13 is a pictorial frontal illustration of the anastomosis completed upon removal of the tubular removal instrument and tying off of the suture ends about the segment of the anastomosis from which the tubular removal instrument is withdrawn.

FIGS. 23a-c are, respectively, side sectional and top and partial perspective views of another seal in accordance with the present invention;

FIGS. 24a-f are perspective views and sectional views of another seal according to the present invention;

FIGS. 30a-c are sectional views of the seal of FIG. 29 during a surgical procedure;

DETAILED DESCRIPTION OF THE INVENTION

Figure 3:
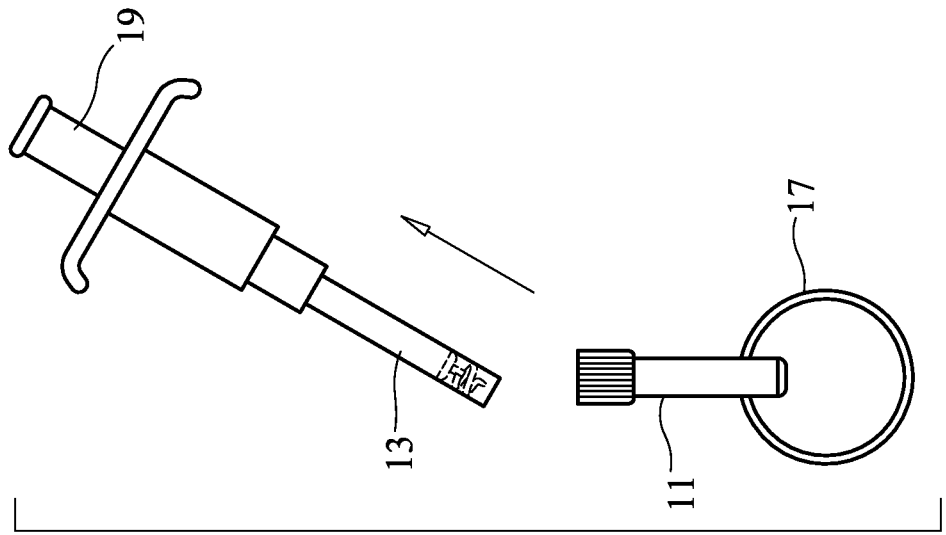
FIG. 3 is a pictorial illustration of the hemostatic sheath positioned within the aorta as the aortic punch is removed.
Figure 2:
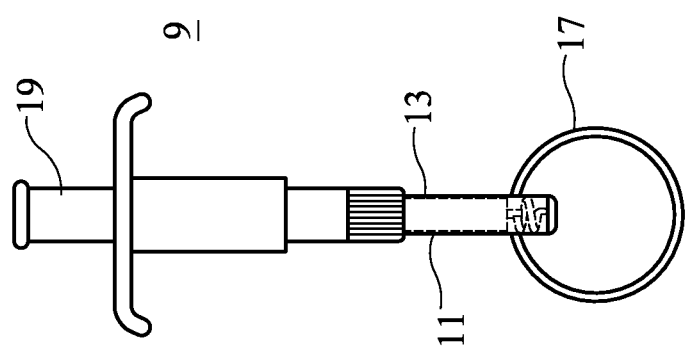
FIG. 2 is a pictorial illustration of the hemostatic sheath penetrated through the aortic wall.
Figure 1:
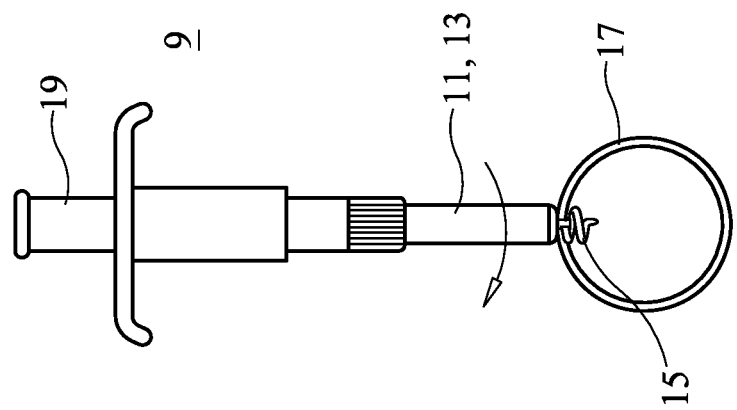
FIG. 1 is a pictorial illustration of the corkscrew aortic punch disposed for insertion into the aorta through a hemostatic sheath in accordance with one embodiment of the present invention.
Figure 15:
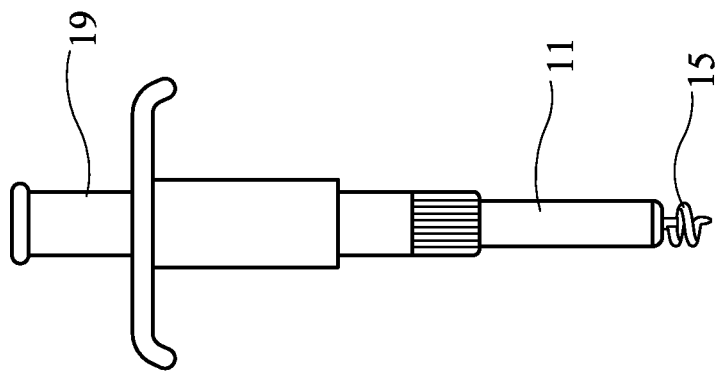
FIG. 15 is a frontal view of the assembled aortic punch and hemostatic sheath prepared for performing an aortotomy according to the present invention.
Figure 14:
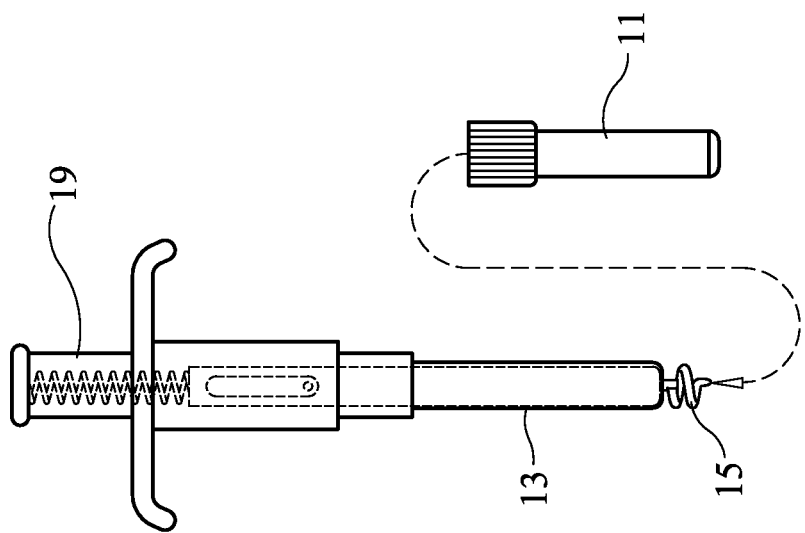
FIG. 14 is an exploded view of the aortic punch and hemostatic sheath in accordance with one embodiment of the present invention.

Referring now to FIGS. 1, 2 and 3, there are shown pictorial views of the aortic punch 9 configured for penetrating the aorta 17 of a patient in preparation for a proximal anastomosis of a bypass vessel to the aorta of the patient. Specifically, an outer hemostatic sheath 11 is coaxially disposed over the lower elongated segment 13 of the aortic punch which supports a corkscrew-type auger 15, as shown in FIGS. 14 and 15. The punch and auger 15 are rotated into a wall of the aorta 17 and the plunger 19 can then be depressed to penetrate the sharpened edge of the lower elongated segment 13 through the aorta wall. The punched-out segment of aorta wall remains captivated on the cork screw 15, and the hemostatic sheath 11 is positioned within the punched hole through the aorta wall. The plunger mechanism 19 and attached elongated lower segment is removed from the hemostatic sheath 11 that remains in position through the aorta wall, as shown in FIG. 3. A fluid-tight seal is included within the hemostatic sheath 11 to inhibit outflow of blood under pressure from the aorta 17 in which it is positioned.

Referring now to the pictorial illustration of FIG. 4, there is shown a seal-insertion instrument 21 that includes a sheath 23 of outer diameter sized to slide within the hemostatic sheath 11, and a plunger 25 that is disposed to slide axially within the sheath 23 for selectively ejecting the hemostatic seal structure 27 from its confinement within the sheath 23. The hemostatic seal structure 27, as later described herein with reference to FIG. 16, includes resilient members that are confined within the sheath 23 in preparation for positioning and expansion into sealing engagement with the aorta wall, as later descried herein.

Referring now to the pictorial illustrations of FIGS. 5 and 6, the seal-insertion instrument 21 is inserted into the hemostatic sheath 11 through the fluid-tight seal therein, and the plunger 25 is depressed to eject a portion of the hemostatic seal structure 27, within the aorta 17. The plunger 25 includes an axial lumen therethrough to pass a length of line 28 that is attached to the hemostatic seal structure 27. The proximal end of plunger 25 may also include a hemostatic seal 100 through which the length of line 28 passes.

As illustrated in FIGS. 6, 7, 16 and 17, a convex or mushroom-shaped sealing element 29 of the hemostatic seal structure 27 is deployed and manually restrained within the aorta 17 covering the punched aortic hole as the hemostatic sheath 11 and the seal-insertion instrument 21 are removed together from the aorta 17. The hemostatic seal structure 27 is thereby liberated from confinement within the seal-insertion instrument 21 to expand into sealing engagement with the aorta wall inside the punched aortic hole.

Figure 16:
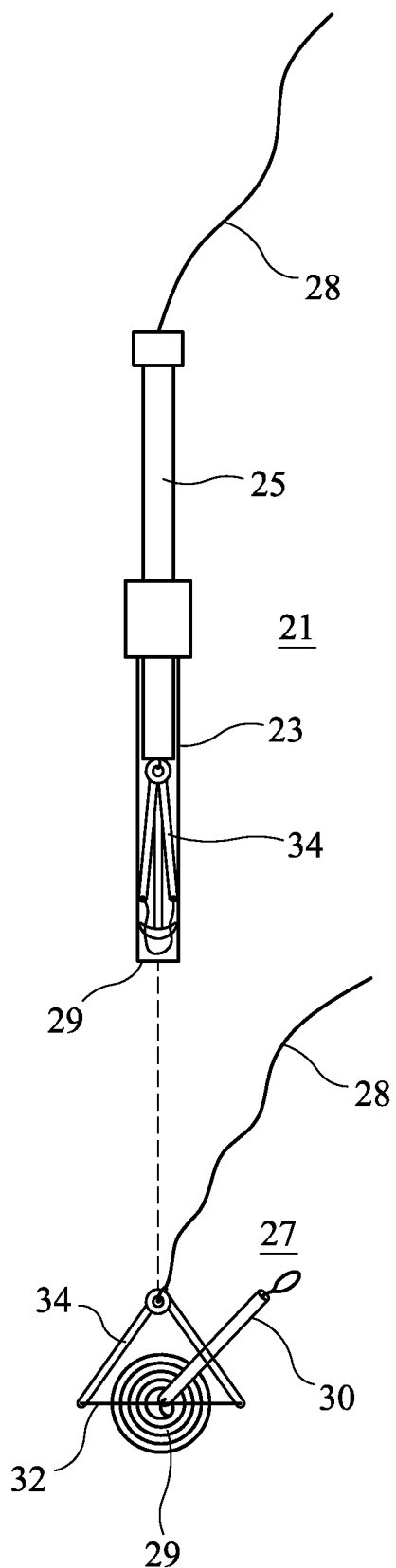
FIG. 16 is an exploded view of the hemostatic seal positioning mechanism that illustrates the hemostatic seal and tensioning structure in deployed condition and in confined condition.

Referring now to FIG. 16, the hemostatic seal structure 27 includes the convex and mushroom-shaped sealing element 29, and this sealing element 29 includes an integral central stem 30 that is attached via a suture tether 32 to a resilient frame 34 which tensions the suture tether 32, and the sealing element 29 has an outer periphery. The resilient frame 34 is attached to the length of line 28 that passes through an axial lumen through the plunger 25 as the entire structure is packed in confined configuration within the hollow sheath 23 of the seal-insertion instrument 21. When ejected from the hemostatic sheath 23 upon depression of the plunger 25, the resilient frame 34 expands to tension the suture tether 32. Manual positioning by the surgeon's finger, as shown in FIG. 7, promotes proper sealing of the hole in the aorta as the resilient frame 34 expands to tension the suture tether 32. As thus positioned in this configuration, the resilient frame 34 maintains tension on the suture tether 32 that, in turn, supports the sealing element 29 from outside the aorta to provide outwardly-directed resilient biasing force on the sealing element 29. This resilient force establishes firm sealing engagement of the sealing element 29 against the inside wall of the aorta. In other words, the resilient frame 34 may be construed broadly as a resilient member that extends laterally and includes a pair of mating ends, as shown in FIG. 16, that are disposed to traverse the periphery of the flange of sealing element 29. As shown in FIG. 16, suture tether 32 (i.e., more broadly construed as a strand of flexible material) is attached to the mating ends and to one of the stem and the flange for supporting the stem and the flange intermediate the mating ends of the resilient member.

In addition, the suture tether 32 greatly facilitates removal of the resilient frame 34, as later described herein, upon simply cutting one or both ends of the suture tether 32 away from the resilient frame 34 for removal from the sealing element 29. In one embodiment the suture-tether 32 may pass through the convex segment of the sealing element 29 to the concave side thereof on both sides of the central stem 30. In another embodiment, the suture tether 32 may be tied to the central stem 30 closely adjacent the concave surface of the sealing element 29.

Figure 17:
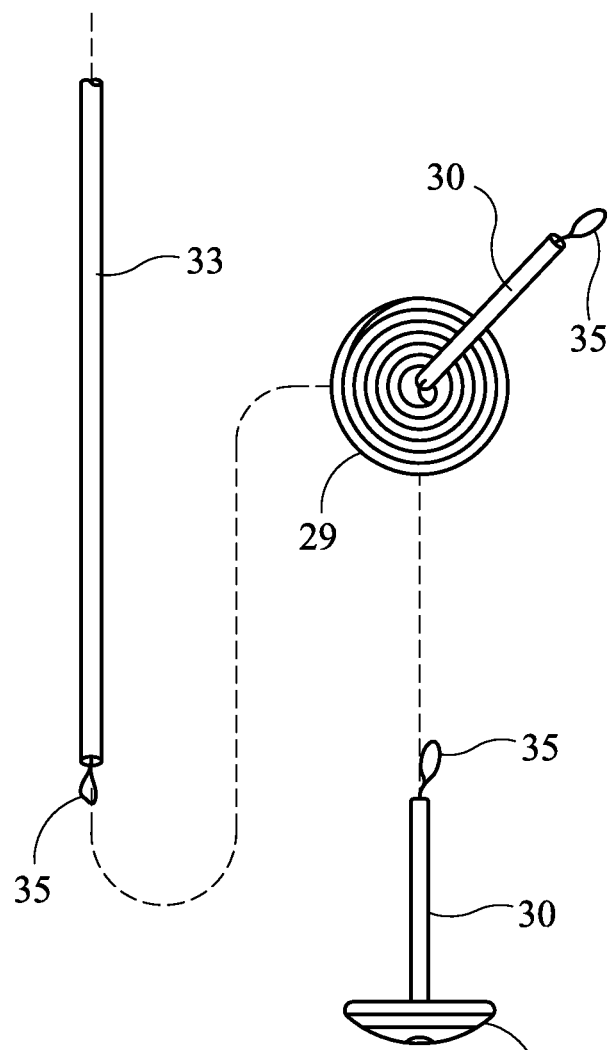
FIG. 17 is a pictorial illustration of the formation of a hemostatic seal in accordance with one embodiment of the present invention.
Figure 18:
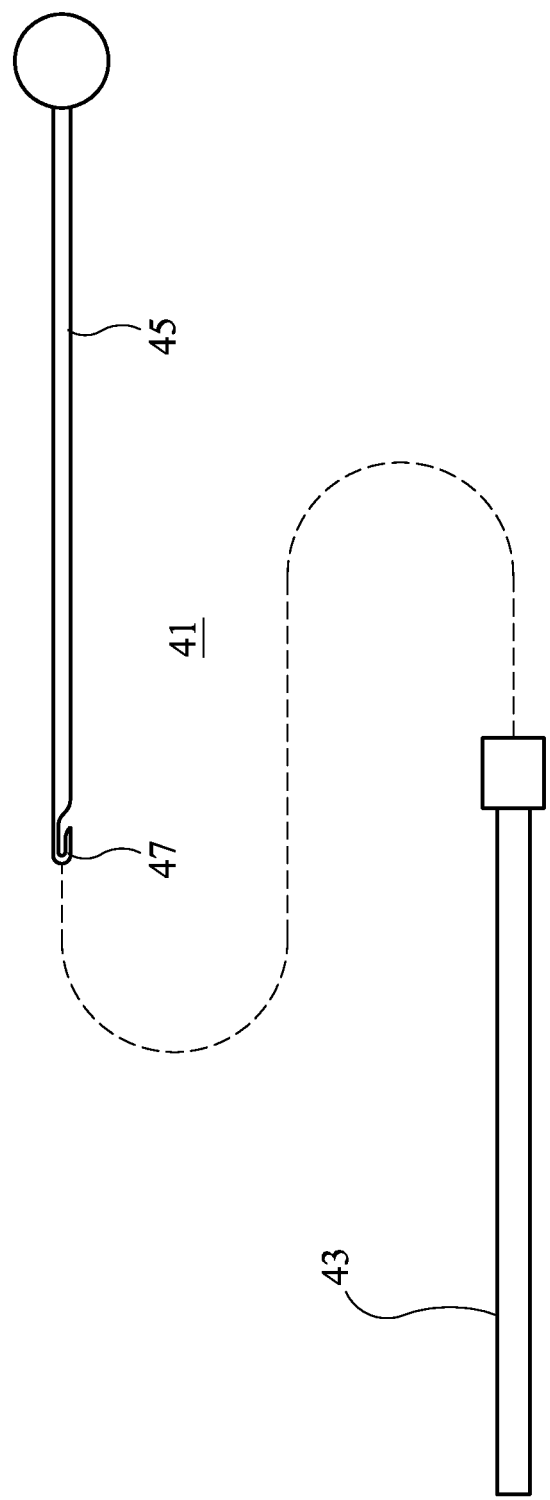
FIG. 18 is a pictorial exploded illustration of a hemostatic seal removal instrument according to one embodiment of the present invention.
Figure 34:
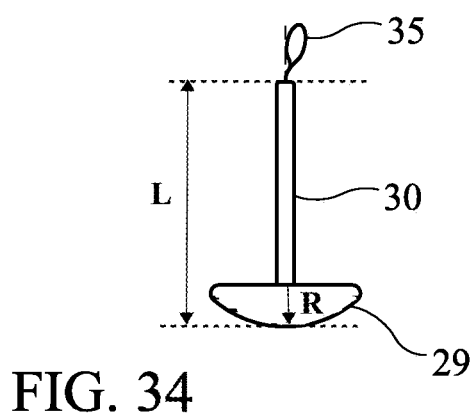
FIG. 34 is an illustration of the sealing element of FIG. 17 and its attached stem.

The sealing element 29 is formed in accordance with one embodiment of the present invention, as illustrated in FIG. 17. Specifically, a hollow tube 33 of flexible material such as polyvinyl chloride, PEBAX, or other polymer material may be extruded about a looped suture 35 or wire or other tensile member for improved tensile strength. Alternatively, a solid, flexible rod of similar material having sufficient tensile strength may be used. The hollow tube (or solid rod) 33 may be helically or spirally wound into the configuration of the mushroom-shaped sealing member 29, with the central stem 30 integrally formed thereon. As evident from FIG. 34, the concave mushroom-shaped sealing element 29 comprises flange of a radius R and the stem 30 has a length L that extends within the outer periphery and beyond the radius R of the concave surface of the sealing element 29. The central stem 30 is linear, straight, yet flexible. The adjacent convolutes of the spirally-wound tube 33 with suture 35 or other tensile member disposed therein (or solid rod) may be lightly adhered together through the application of heat and pressure to a thermoplastic material, or through other suitable adhesive attachments to form the substantially fluid-impervious sealing element 29 that is flexible and resilient for confined packing within the hollow sheath 23 of the seal-insertion instrument 21. Light adhesion between adjacent convolutes of the spirally-wound tube 33 with a suture therein (or solid rod) promotes disassembly of the sealing element 29 as by tearing along the boundary (i.e. a continuous region of diminished shear strength) between adjacent convolutes under tension applied to the central stem 30, as later described herein. It should be noted that the central stem 30 is an integral and continuous portion of the spiral convolutes (or other meandering pattern) that extend continuously from the central stem portion 30 to the outer perimeter (outer periphery) of the mushroom-shaped portion of the sealing element 29. This assures substantially uniform high tensile strength of the hollow tube 33 with suture 35 disposed therein (or solid rod) over the entire continuous length of the tube 33 to assure complete removal from the aorta in the manner as later described herein. In one embodiment, the sealing element 29 may be formed by winding the hollow tube 33 (or solid rod) around a mandrel that includes separable flanges which are axially spaced apart by about the diameter dimension of the tube 33 (or solid rod), and that includes a central hollow support to house the portion that forms the central stem 30. Heat and pressure applied between such flanges causes thermoplastic flow and adhesion between adjacent convolutes in the mushroom-shaped portion and to the stem 30 in the central portion of the fluid-impervious sealing element 29 thus formed. Alternatively, bioinert adhesive may be applied to the convolutes and central stem 30 to retain the shape of the fluid-impervious sealing element 29 thus formed.

Figure 11:
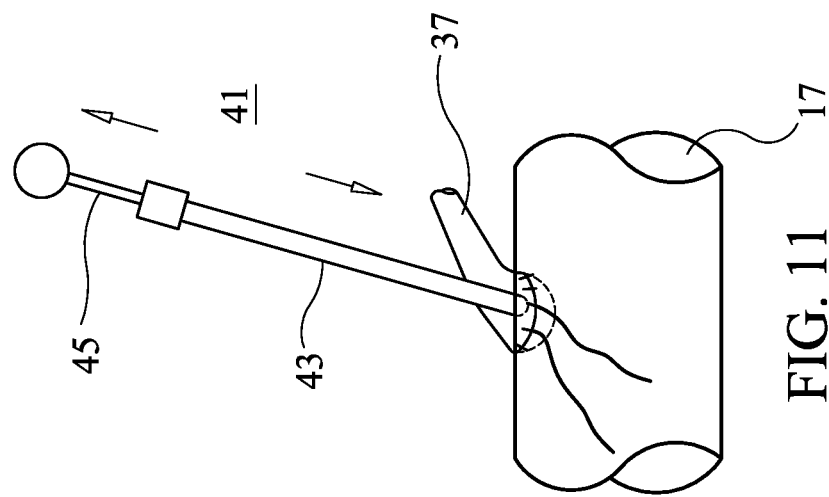
FIG. 11 is a pictorial frontal illustration of the tubular removal instrument disposed over the stem of the hemostatic seal in preparation for removal from the graft site.
Figure 10:
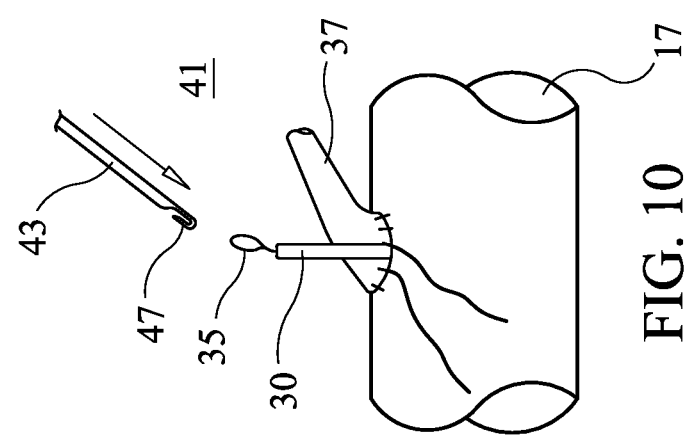
FIG. 10 is a pictorial frontal illustration of the suture anastomosis substantially completed with the stem of the hemostatic seal positioned near the last stitches.

Referring now to the pictorial illustration of FIG. 8, the sealing element 29 is shown disposed in sealing position inside the punched aortic hole with the integral stem 30 protruding through the hole, and with suture loop 35 protruding from the proximal end of the stem 30. It should be noted that the resilient frame 34 and the suture tether 32 are positioned on the outer wall of the aorta to exert an outwardly-directed force on the sealing element 29 to retain it in sealing engagement with the inner aortic wall, and to prevent inadvertent expulsion of the sealing element 29 from the hole or loss of the sealing element 29 into the aorta. The sealing element 29 is thus maintained in sealing position over the hole in the aorta during formation of the proximal anastomosis by suturing the graft vessel 37 onto the aorta 17, as shown in FIGS. 9-11. The stem 30 is flexible and can be gently pushed out of the way of sutures that are stitched about the hole in the aorta and into the proximal end of the graft vessel 37. In this way, the stem 30 is left protruding through the anastomosis at a position thereon near the last stitch (or between any adjacent stitches). Stem 30 may be construed as a locator, as shown in FIGS. 7, 8 and 9, that is part of the fluid-impervious flange of the sealing element 29 having an outer periphery, wherein the stem 30 may protrude through the hole in the aorta (i.e., more broadly construed as an aperture in the wall of a fluid conduit of a patient), wherein the stem 30 may serve to position the flange against an inner wall of the fluid conduit, such as the aorta, and over the aperture (i.e., hole in the aorta). Thus, stem 30, which may be construed as a locator on the flange, extends to a conduit outer wall beyond the aperture for providing force on the flange against the inner wall of the conduit, as shown in FIGS. 7, 8 and 9.

Referring now to FIGS. 10-12 and 18, a seal-removal instrument 41 includes an outer tube 43 with an inner core 45 that is slidable within the outer tube 43 and that carries a hook 47 at its distal end. The assembly of inner core 45 disposed within the outer tube 43 is positioned over the stem 30 of the sealing element 29 with the hook 47 engaged in the suture loop 35. The outer tube 43 is positioned onto the stem 30 down to the root of its attachment to the mushroom-shaped spiral-wound sealing element 29, and the inner core 45 is then withdrawn from the outer tube 43. These motions cause the spirally-wound convolutes of the sealing element 29 to tear and otherwise disassemble for convenient removal as a continuous strand 29', as shown in FIG. 12, of the material from which the spirally-wound sealing element 29 was formed. Thereafter, the outer tube 43 may be withdrawn and the sutures tied off near where outer tube 43 was positioned to complete the proximal anastomosis, as shown in FIG. 13.

Alternatively, the central stem 30 may be formed as an integral part of the mushroom-shaped portion of the sealing element 29 with sufficient length to extend through the outer tube 43 adequately to permit finger gripping of the stem 30 for manual tensioning and removal of the continuous strand 29' through the outer tube 43 without the need for the hooked inner core 45 and associated suture loop 35.

Figure 19:
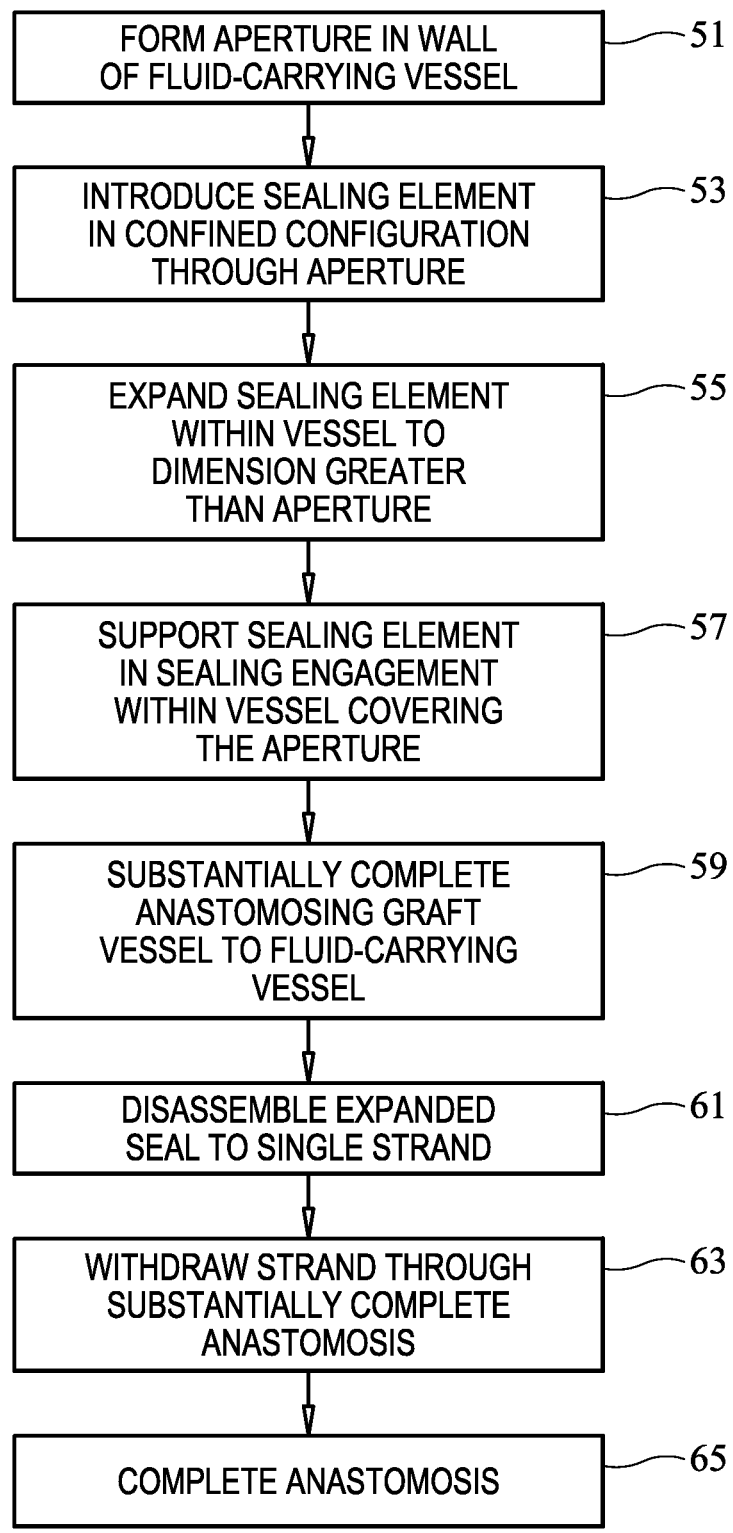
FIG. 19 is a flow chart illustrating an embodiment of the surgical process according to the present invention.

Referring now to the flow chart of FIG. 19, an embodiment of the surgical procedure performed according to the present invention includes forming an aperture 51 in the aorta wall, as illustrated in FIGS. 1 and 2. The hemostatic seal structure in confined configuration within the hemostatic sheath is then introduced 53 into the aorta through the hole in the wall thereof. The sealing element resiliently expands 55 inside the aorta to form a fluid-tight seal over the hole in the wall, and is supported 57 on a tensioned tether from the outside of the aorta. A central stem portion of the sealing element is sufficiently flexible to be pushed away from the locations on the aorta at which suture stitches are inserted during substantial completion 59 of anastomosing the graft vessel to the aorta over the hole in the wall thereof. The central stem portion of the sealing element thus protrudes through the anastomosis between adjacent stitches and is accessible to facilitate removal of the sealing element disposed within the aorta beneath the anastomosis. The sealing element is removed through a tube that is positioned over the central stem portion by applying tensile force to the central stem portion relative to the tube. This disassembles or unravels the sealing element into a single strand 61 that is removed through the tube 63, as shown in FIG. 12. The ends of the suture adjacent to the location on the anastomosis through which the strand was removed may then be tied off to complete the anastomosis 65.

Figure 20:
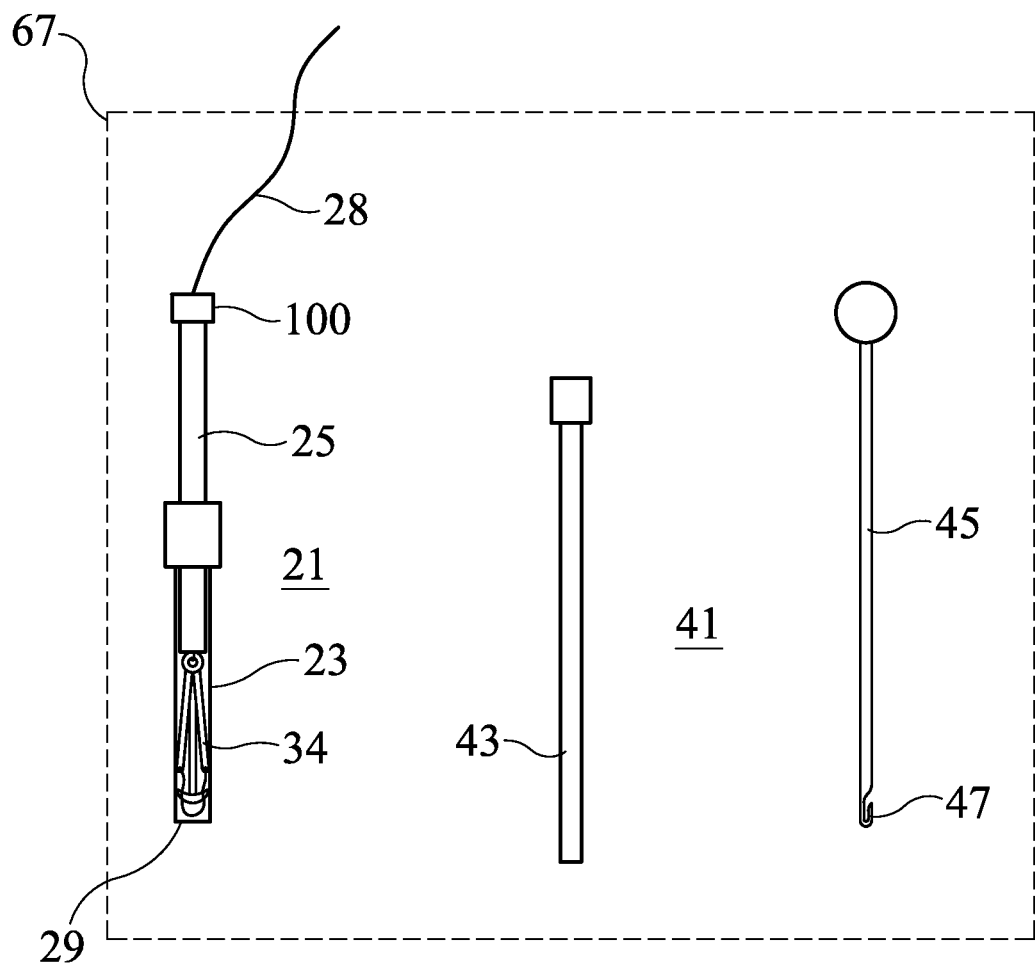
FIG. 20 is a pictorial illustration of a sterile kit of the instruments for performing the surgical process according to the present invention.

Referring now to FIG. 20, there is shown a pictorial illustration of a kit of instruments and components suitable for performing the surgical procedure according to the present invention, as previously described herein. Specifically, at least the seal-insertion instrument 21 and seal removal tube 43 are packaged within a sealed enclosure 67 that preserves a sterile environment and facilitates convenient shipping and handling of these components without contamination or damage. Additionally, a hemostatic sheath 11 may be included within the enclosure 67 for use with a punch (separately available to a surgeon) in the manner as previously described herein with reference to FIGS. 1 and 2.

Figure 21A:
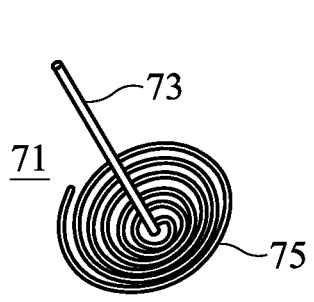
FIGS. 21a and 21b are pictorial illustrations of other forms of temporary aortic seal in accordance with other embodiments of the present invention.

Referring now to FIG. 21a, there is shown a perspective view of a frame 71 for a seal in accordance with another embodiment of the present invention. In this embodiment, the frame 71 may be formed as a spiral of resilient material such as nitinol that extends along a continuous path from the central region of the attached stem 73 to an outer substantially circular periphery 75. This frame 71 may then be covered with a thin film or layer of fluid impervious material such as silicone or latex rubber covering adjacent convolutes to form a mushroom-shaped sealing element that can be disassembled between adjacent convolutes and removed as a single strand in the manner as previously described herein. Alternatively, the frame portion 75 may be thermally set with adjacent convolutes in contact with each other to form a seal which can be disassembled as previously described herein. In one embodiment, the shape-memory characteristics of Nitinol facilitate formation of a frame portion 75 coated with a thin-film of flexible impervious material that exhibits an initial, contracted state with adjacent convolutes in substantial contact at ambient or room temperature. Once inserted into a vessel in contact with blood at the normal elevated temperature the frame portion expands into the functional mushroom-shaped sealing element, as previously described herein.

Figure 21B:
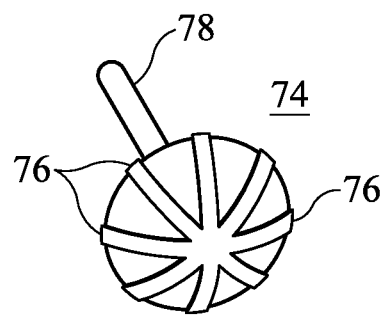

Referring now to FIG. 21b, there is shown a frame 74 including a plurality of flexible, resilient ribs 76 that extend radially from, and are attached to a base of, the central stem 78. The ribs 76 are covered with a thin film or layer of a fluid impervious material, for example as previously described, to form a mushroom-shaped sealing element that can be disassembled by reconfiguring the ribs 76 into alignment with the central stem 78 from the base thereof. Alternatively, the mushroom-shaped sealing element as illustrated in FIG. 21b may be formed as a homogeneous structure of ribs 76 and impervious layer, for example, of silicone rubber of various thicknesses throughout to inhibit inversion of the sealing element under pressure of blood in a vessel sealed by such element. Specifically, the mushroom-shaped sealing element 74 promotes formation of a fluid-tight seal between the perimeter thereof and the inner, substantially cylindrical wall of the target vessel, and also establishes a space about the central stem 78 for convenient passage of the suture needle through the vessel wall about the stem while a fluid seal is maintained at a greater distance from the stem. An inversion of the convex or mushroom-shaped sealing element under the pressure of blood in the vessel is to be avoided because of the diminished resultant space that is thus provided about the stem for suture stitching, and because of the resultant poorer fluid seal that is formed within the vessel.

Figure 22A:
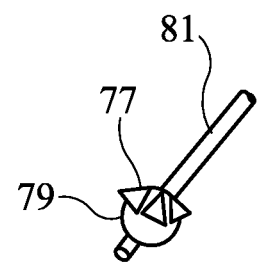
FIG. 22a is a perspective view of an inflatable, skirted seal according to another embodiment of the present invention.

Referring now to FIG. 22a, there is shown a perspective view of another seal according to the present invention including a segmented skirt 77 of flexible material such as silicone rubber overlaying an inflatable balloon 79. The skirt and balloon are symmetrically disposed about a central tube 81 that supplies fluid under pressure to the balloon 79. In operation, this embodiment of a temporary seal in the aorta during formation of a proximal anastomosis facilitates insertion into an aperture in the aorta in an uninflated, constricted condition. In this condition, the skirt 77 overlaying the balloon 79 and including a plurality of resilient segments disposed approximately in axial alignment with the central tube 81 presents a sufficiently small cross section to be inserted through an aortic aperture. The balloon 79 is then inflated to expand the segments of the skirt 77 radially outwardly from the central tube 81 to thereby seal the aortic aperture and provide a shield for the balloon 79 during suturing of a graft vessel about the perimeter of the aortic aperture. Prior to completion of the anastomosis, the balloon 79 may be deflated to return the segments of skirt 77 substantially to axial alignment along the central tube 81 for easy removal through the anastomosis before completion of the suturing.

Figure 22B:
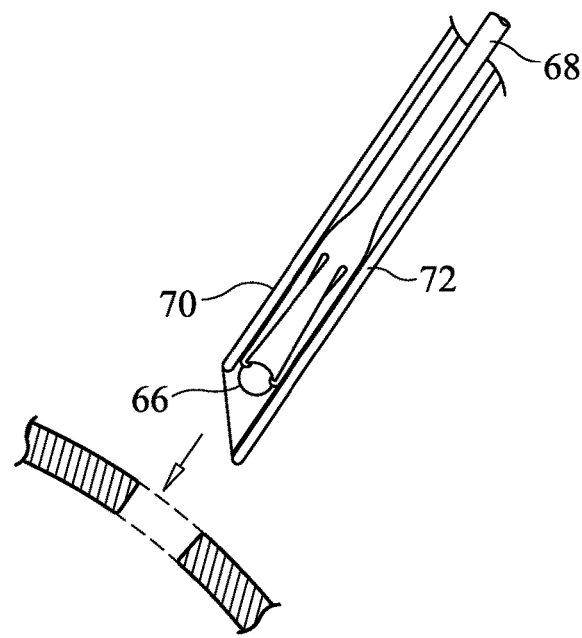
FIGS. 22b-e are pictorial sectional views of another skirted seal and associated procedures according to the present invention.
Figure 22C:
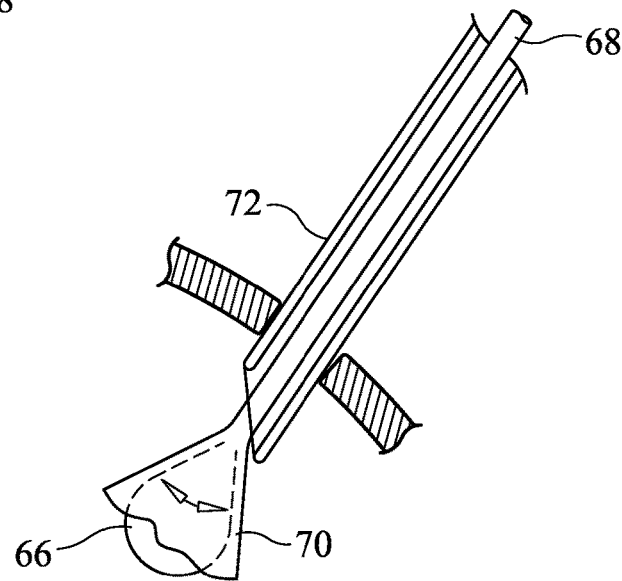
Figure 22D:
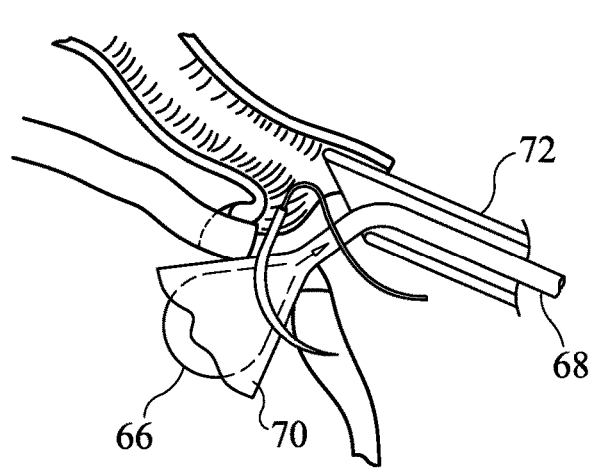
Figure 22E:
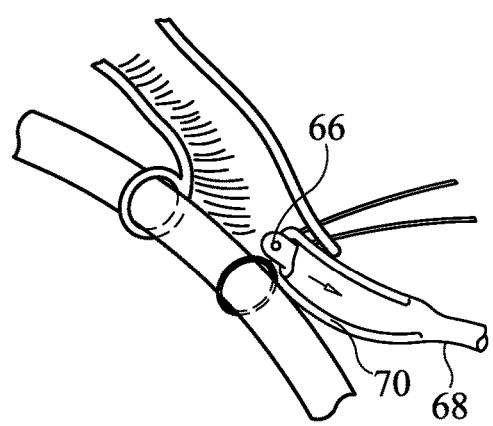
Figure 24C:
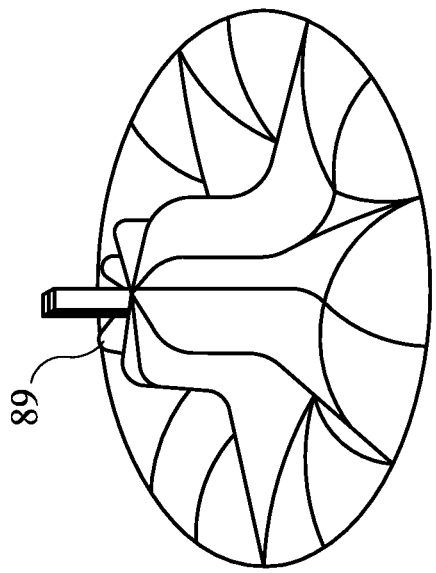
Figure 24B:
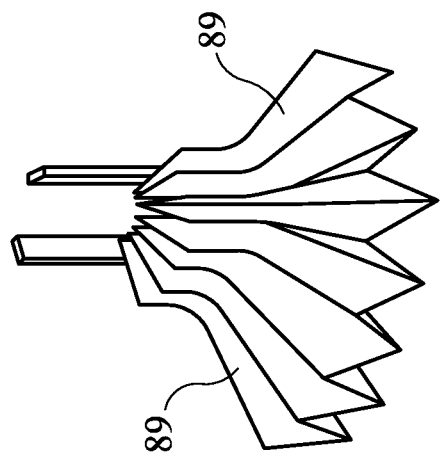
Figure 24F:
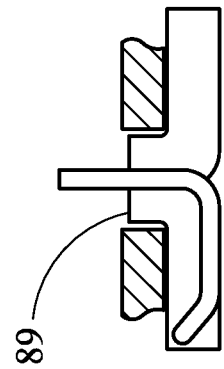
Figure 24E:
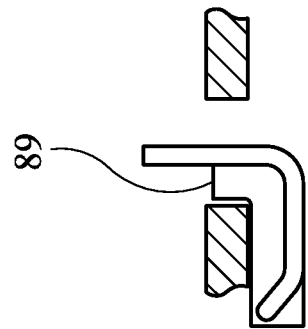
Figure 24D:
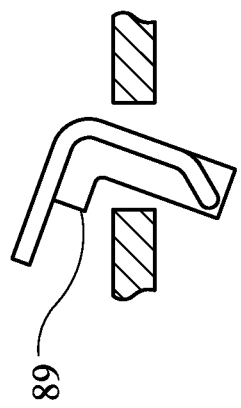

In another embodiment of a skirted seal, as illustrated in FIGS. 22b-c, there is shown a folded, flexible cone 70 with the apex thereof disposed about the distal end of the flexible tube 68 that communicates with balloon 66. The assembly is collapsed in uninflated and unextended condition within the hollow bore of an aortotomy punch, or other insertion tube, 72 for positioning within the vessel through the aortic wall. As illustrated in FIGS. 22c and 22d, the balloon 66 is then inflated with fluid under pressure supplied via tube 68 to expand the skirt of the flexible cone 70 to a dimension greater at the outer rim than the dimension of the aperture in the vessel wall. The insertion tube 68 may be withdrawn from the aperture in the vessel wall to be used in skew orientation to the initial alignment, as shown in FIG. 22d, to assist in tensioning the flexible tube 68. In this way, the deployed and expanded cone 70 can be retained in tension against the inner periphery of the aortic aperture as suture stitching of a graft vessel proceeds about the aperture. First and last suture stitches, or some segment of an incomplete anastomosis of a graft vessel to the aorta, remain open or loose to facilitate removal of the cone 70 and balloon 66 and the tube 68, as shown in FIG. 22e. Specifically, after the suture stitches are positioned about the periphery of the aperture and about the tube 68, the balloon is deflated and the skirt of the cone 70 is thereby collapsed for easy withdrawal through the incomplete segment of the anastomosis, and the stitches are thereafter cinched and tied off to complete the procedure with negligible loss of blood.

Referring now to FIGS. 23a-c, there are shown embodiments of other temporary seals according to the present invention. Disc 83 is formed of several raised resilient segments 85 attached to a peripheral ring 87 that may be collapsed to a dimension sufficiently smaller than an aortic aperture to facilitate easy installation with the peripheral ring 87 disposed within the vessel, and with the raised inner segments protruding through the aperture under the pressure of blood within the vessel. The protruding inner segments thus retain the sealing element 83 in place covering the aortic aperture with reduced probability of being displaced from that position by blood flowing under pressure in the aorta. The sealing element 83 may thereafter be distorted or otherwise collapsed for removal from its sealing position through an incomplete segment of an anastomosis, as previously described herein.

In a similar embodiment, as illustrated in the top and side sectional views of FIGS. 23b and 23c, respectively, a flexible peripheral ring 87 may be integrally formed with protruding inner segment 85 for attachment to the external wall of the aorta using adhesive or clips or temporary sutures, or the like, with the protruding inner segments configured to be disposed within the aperture to form a temporary seal.

In the embodiment of a temporary seal illustrated in FIGS. 24a-f, a generally L-shaped configuration of pleated and folded flexible membrane 89 is disposed to be inserted through an aortic aperture and thereafter unfolded in a circular pattern to form an impervious seal within the aortic aperture in engagement with the internal walls of the aorta. Removal from within the aorta is facilitated by re-folding the membrane 89 back to its original L-shaped configuration for removal through a partially-completed anastomosis in the manner as previously described herein.

Figure 25A:
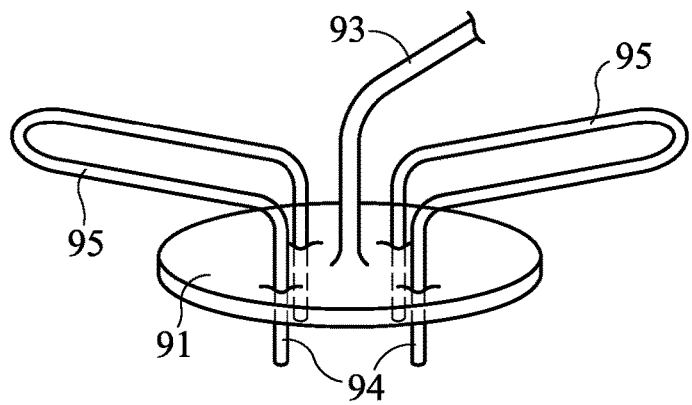
FIGS. 25a-e are perspective and sectional views of another embodiment of a seal according to the present invention.
Figure 25B:
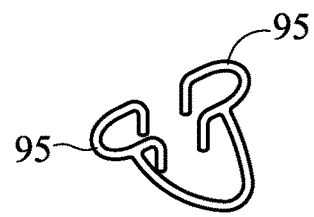
Figure 25C:
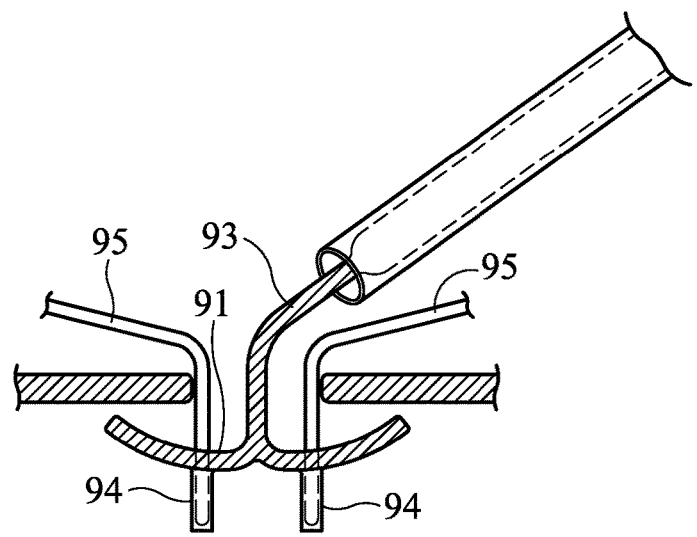
Figure 25E:
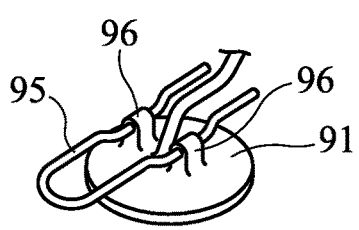
Figure 25D:
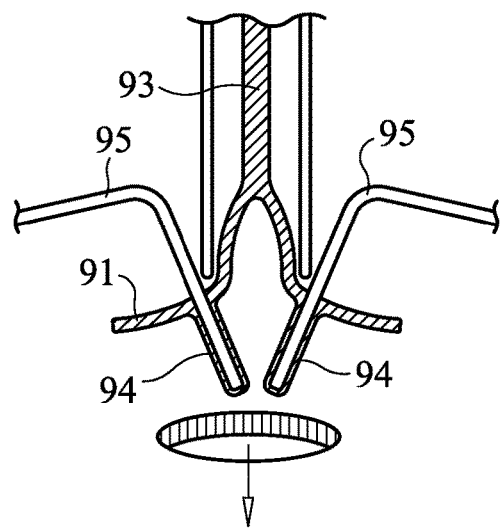

Referring now to FIGS. 25a-e, there are shown various configurations of temporary seals that may be conveniently positioned in and removed from an aortic aperture. Specifically, the resilient plate 91 includes a central stem 93 and a plurality of sockets or recesses 94 disposed in the plate 91 about the central stem 93 to receive one or more centering arm(s) 95 within the sockets 94. In this configuration, the arm, or arms, 95 within the sockets 94 may be manipulated manually to bend or deform the resilient plate 91 into a diminished configuration, as shown in FIG. 25d, that may be conveniently inserted into the aortic aperture. In addition, the arms 91 inserted in the sockets 94 protrude upwardly through the aortic aperture and outwardly over the exterior of the aortic wall, as shown in FIG. 25c, both to assure centering of the plate 91 within the aperture, and to assure that the plate 91 remains at the site and is not carried away in aortic blood flow. Alternatively, the plate 91 may include stanchions 96, as shown in FIG. 25e, spaced symmetrically about the central stem 93 on the top surface, and including lateral holes therein through which the arms 95 extend for convenient insertion and removal of the assembly from within an aortic aperture.

Figure 26A:
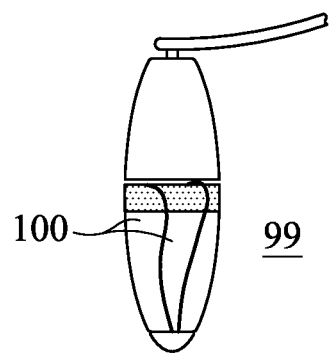
FIGS. 26a-e are respectively sectional views of an expandable seal according to another embodiment of the present invention.
Figure 26B:
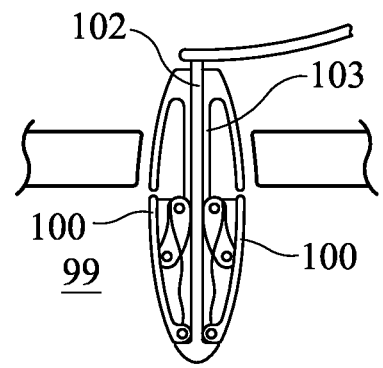
Figure 26C:
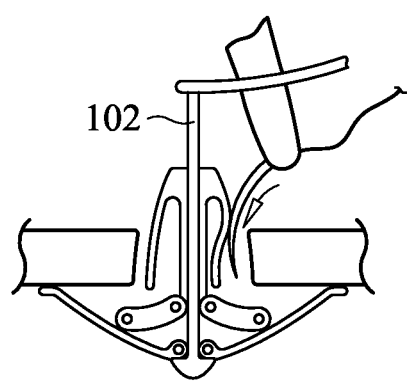
Figure 26D:
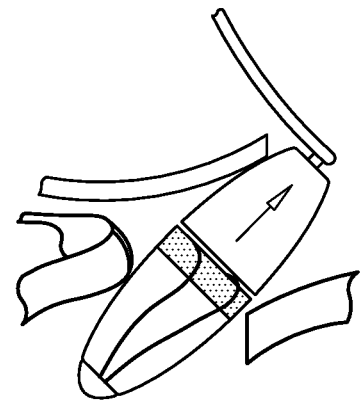
Figure 26E:
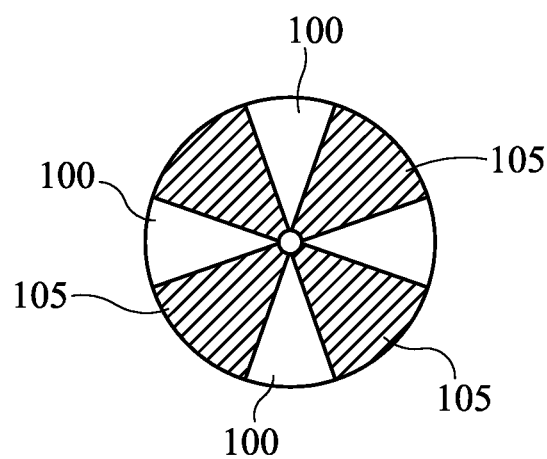

Referring now to FIGS. 26a-e, there are shown sectional views of another embodiment of a temporary seal 99 that is manually reconfigurable within an aortic aperture to extend lower segments 100 radially outwardly from a central stem 103. The extension of segments 100 is actuated by axial motion of the central rod 102 relative to stem 103 via the linkage between the two elements. The segments carry flexible membranes 105 between segments 100 to form a substantially continuous hemisphere with a flexible-perimeter to follow inter-aortic contours, as shown in FIG. 26e, to thereby form a liquid-impervious seal against the inner aortic wall. The outer flange of stem 103 is flexible to form an initial seal against the cut edge of the aortotomy before segments 100 are deployed. The flexible outer flange of stem 103 can be deflected away from the cut edge of the aortotomy to permit a suture needle to pass during formation of an anatomosis. The segments thus deployed, as shown in FIG. 26c, also serve as a shield and guide during suturing of a graft vessel to the aorta. The segments 100 may be retracted toward the central stem 103 to form a unit of smaller cross section for removal from the site through a partially-completed anastomosis, as shown in FIG. 26d.

Referring now to FIGS. 27a-d, there is shown another embodiment of a temporary seal according to the present invention in which an insertable boot 111 includes an adhesive outer ring 113 for temporary attachment to the outer wall of an aorta. Specifically, the boot 111 includes a flexible membrane 115 that is attached to and descends from the outer ring 113 for insertion into an aortic aperture. The membrane 115 includes a lateral passage 117 that is sealed in fluid-tight engagement with a lower portion of the membrane 115 formation of and through which the aortic punch is located. This relation between the punch and the ring assures proper insertion of the seal into the aortic aperture immediately following the aperture by the punch. A push wire 119 is disposed about the passage 117 within the confines of the membrane to provide a convenient retrieval mechanism, as later described herein.

The upper perimeter edge of the membrane 115 includes radially inward depressions 121 through which suturing is accomplished, and includes adhesive for temporary attachment to the outer aortic wall. Additionally, the ring 113 is configured as one or more peel-away layers to facilitate positioning the upper perimeter edge of the membrane 115 about an aortic aperture.

Figure 27C:
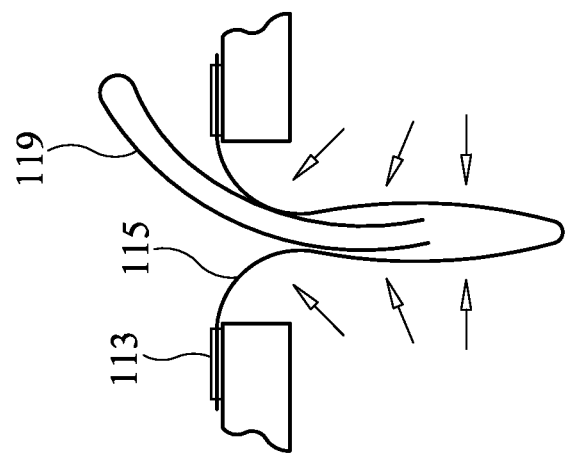
FIGS. 27a-d are perspective and sectional and top views of another embodiment of a seal according to the present invention.
Figure 27B:
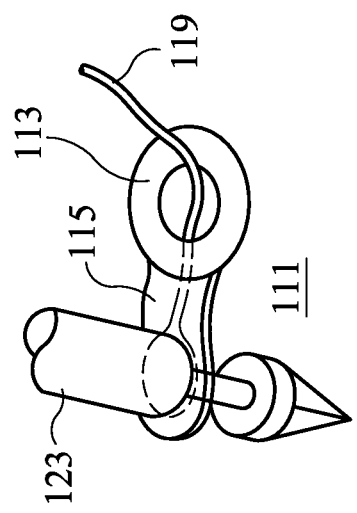
Figure 27A:
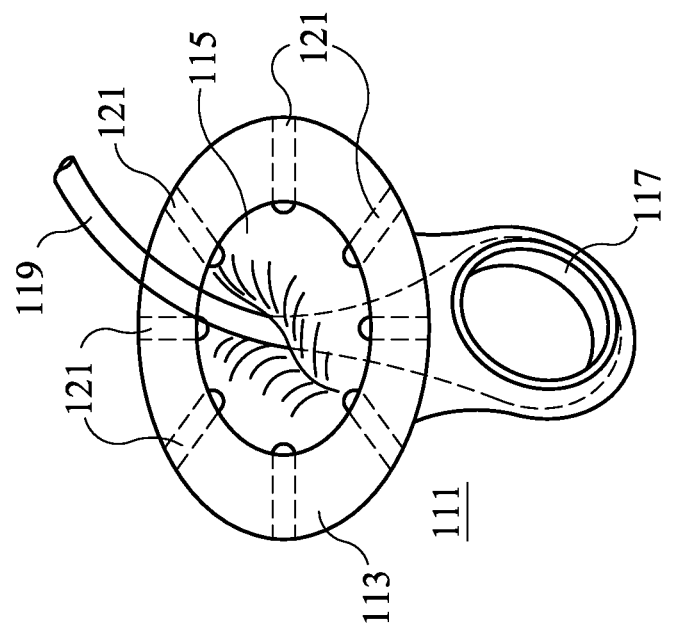

In operation, this embodiment of a temporary seal shown in FIG. 27a is disposed on an aortic punch 123, as shown in FIG. 27, with the punch 123 positioned through the passage 117 to carry the boot assembly 111 into an aperture formed in an aortic wall. As the punch is withdrawn, the push wire 119 is manipulated to insert the lower end of the boot 111 into the aperture thus formed, and the outer ring 113 is substantially centered about the aperture for adhesive attachment of the upper outer edge to the outer aortic wall, as shown in FIGS. 27c, d. The outer ring 113 may be peeled away to leave the slotted upper perimeter edge of the membrane 115 adhered to the outer wall of the aorta. Suturing of a graft vessel over the aortic aperture penetrates the aortic wall through the depressions 121 without penetrating the membrane 115. Upon partial completion of the anastomosis, wire 119 is tensioned to invert the membrane 115 as the passage 117 secured to wire 119 is pulled through an incomplete segment of the anastomosis between stitches, and as the upper adhesive edge of the membrane is released from the outer wall of the aorta. Thereafter, the sutures may be tightened to complete the proximal anatomosis with negligible loss of blood.

Figure 27E:
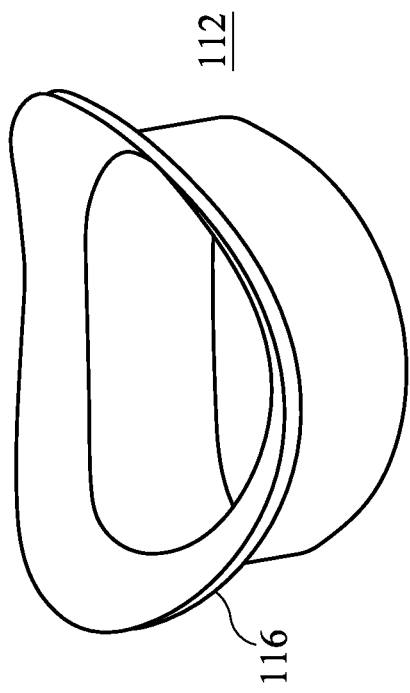
FIGS. 27e-g are perspective views of other embodiments of seals according to the present invention.
Figure 27G:
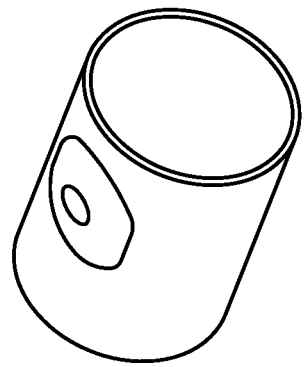
Figure 27D:
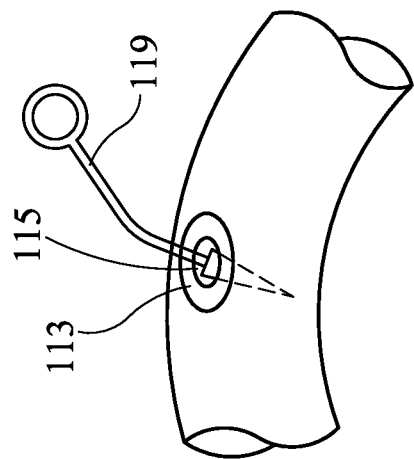
Figure 27F:
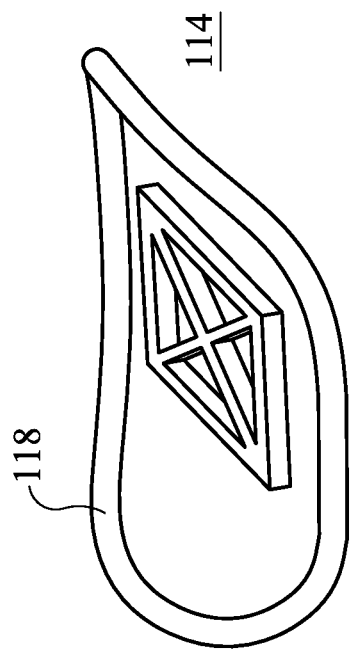

Referring now to FIGS. 27e-g there are shown perspective views of other sealing elements in accordance with alternative embodiments of the present invention. Each of these sealing elements 112, 114 is formed of resilient, flexible material such as silicone rubber for temporarily sealing an aortic aperture. An outer perimeter edge 116, 118 of each sealing element is disposed to form a fluid-tight seal against the inner wall of the aorta as the sealing element 116, 118 is retained in place under resilient tension from outside the aorta in a manner, for example, as previously described herein. Such resilient sealing elements may thereafter be collapsed or otherwise reconfigured for removal through an incomplete segment of an anastomosis, as previously described herein. Specifically, the temporary seal 112 includes an outer perimeter edge 116 that is configured to conform to the generally cylindrical inner wall of the aorta, with the maximally-elevated portions of the perimeter edge 116 oriented upstream and downstream of an aortic aperture. The flexible flange inward from the perimeter edge 116 promotes formation of a fluid-tight seal against surface irregularities of the inner wall and the descending volume from the inner edge of the flange to the lower region of the sealing element provides ample space for manipulating a suture needle during stitching of an anastomosis. Retention of the sealing element 112 covering an aortic aperture is aided by an external tensioning device that tethers the element in place, as described herein.

In similar manner, the embodiment of a temporary sealing element 114 as shown in FIG. 27f includes a perimeter edge 118 that is configured to form a fluid-tight seal against the inner wall of the aorta, as shown in the perspective view of FIG. 27g, with the maximally-elevated portions of the perimeter edge 118 disposed upstream and downstream of an aortic aperture. The 'X'-shaped pattern integrally formed in the sealing element 118, as illustrated in FIG. 27f provides increased rigidity against leak-inducing distortion or expulsion of the sealing element 118 through an aortic aperture under pressure of blood flowing in the aorta. Retention of the sealing element 118 covering an aortic aperture is aided by an external tensioning device that tethers the element in place, as described herein.

Referring now to FIGS. 28a-28e, there are shown other tethered sealing assemblies including a disk 125 and one or more tethers 127. In the embodiment illustrated in FIG. 28e, resilient tethers 127 are affixed to an outer ring 129. In this embodiment of a temporary sealing element according to the present invention, the disk 125 seals an aortic aperture from inside the aorta, and is centered and retained in place covering the aperture by the resilient tethers 127 that are anchored to the disk 125 near central locations. The tethers 127 are tensioned as attached to the outer ring 129 to assure centering and support from outside the aorta for the disk 125 placed inside the aorta. The resilient, flexible disks 125 in these embodiments may be deformed to sufficiently small dimension to facilitate insertion through an aortic aperture for forming a temporary seal therewith. Specifically, the flexible disks 125 of FIGS. 28a-d may be tethered and externally tensioned for retention in sealing engagement over an aortic aperture in the manner, for example, as illustrated in FIGS. 28f-28i. In general, a tensioning device such as the resilient frame 34 carries a tether 32 between resilient arms that exerts a tensile force through the aperture on a sealing element attached to the tether inside the aorta. Attachment mechanisms and stiffening structures integral with the sealing element aid in supporting the sealing element in sealing engagement covering an aortic aperture, and in preventing inversion or blow-out of the sealing element through the aortic aperture.

Figure 28A:
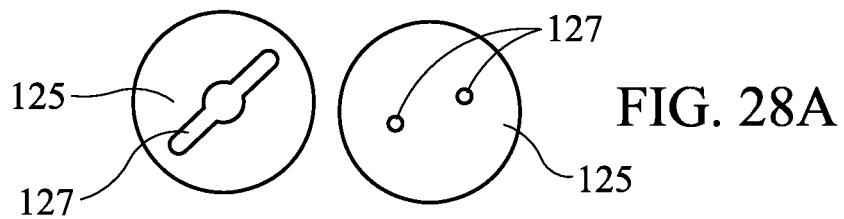
FIGS. 28a-28e are plan views of embodiments of tethered seals in accordance with other embodiments of the present invention.
Figure 28B:
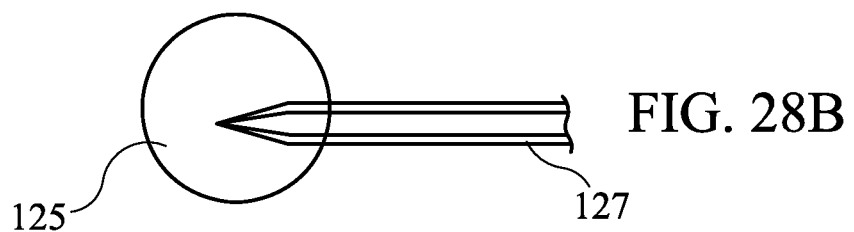
Figure 28C:
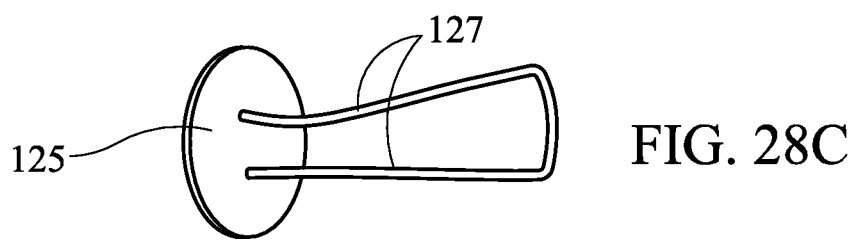
Figure 28D:
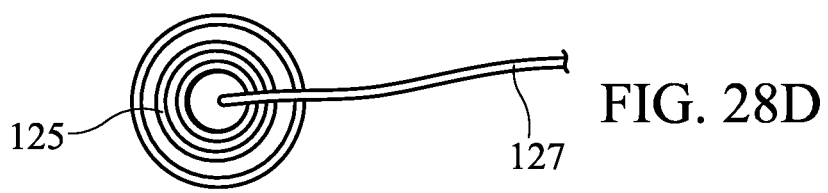
Figure 28E:
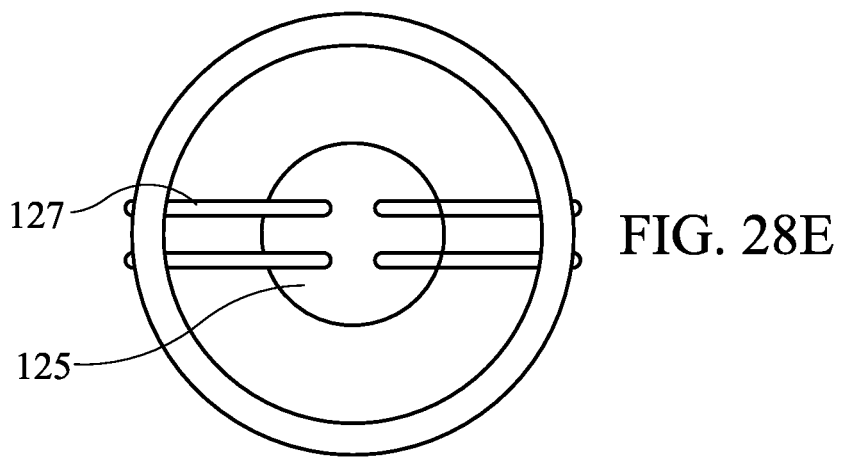
Figure 28F:
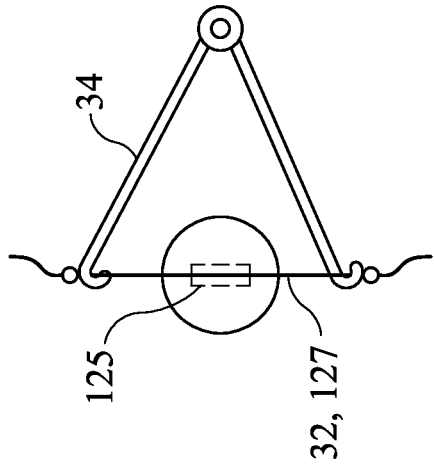
FIGS. 28f-28m are pictorial views of tensioning apparatus and delivery instruments for tethered seals.
Figure 28G:
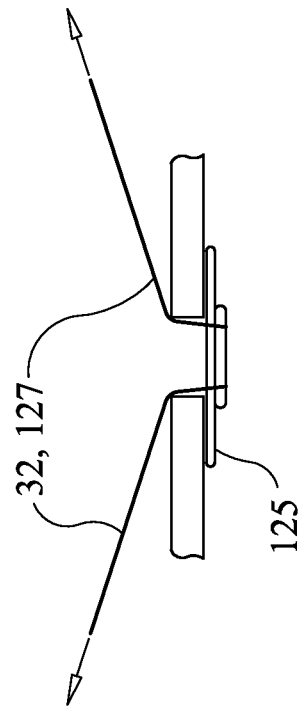
Figure 28H:
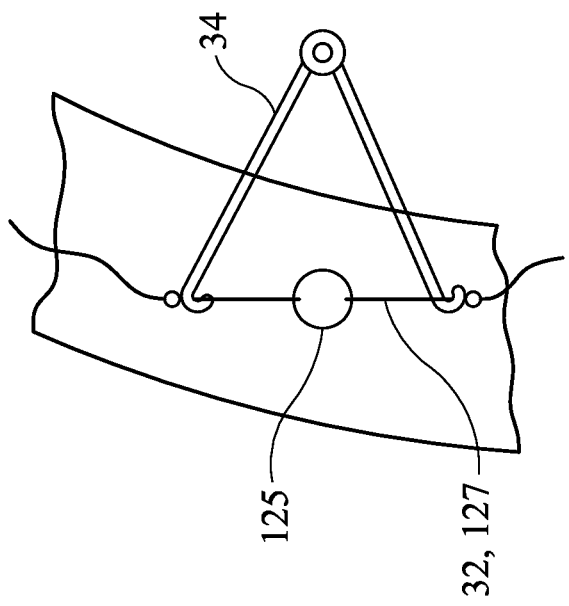
Figure 28I:
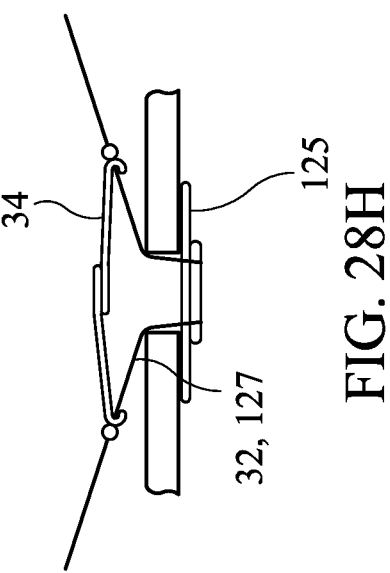
Figure 28M:
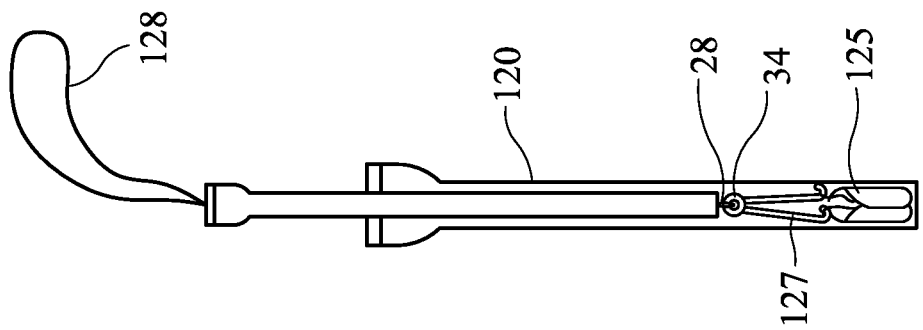
Figure 28L:
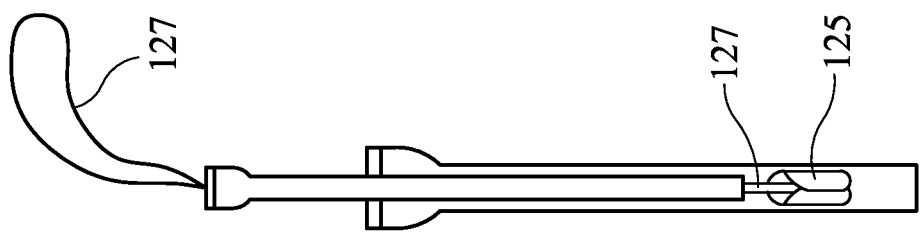
Figure 28K:
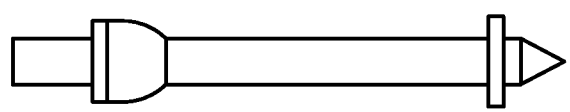
Figure 28J:
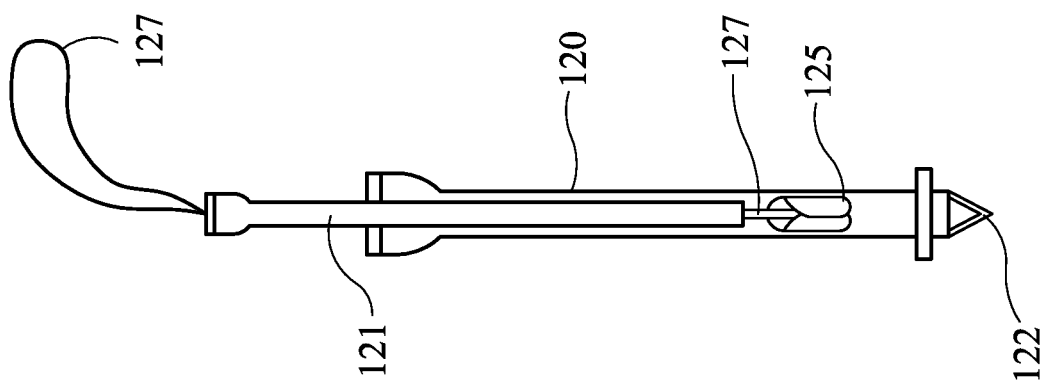

Also, as illustrated in the pictorial views of FIGS. 28j-28m, such flexible disk-shaped sealing elements may be introduced into the aorta through an incision or punched aperture in an aorta in the preparation of an anastomosis of a grafting vessel therewith. Specifically, a combined aortotomy instrument and delivery device as shown in FIG. 28j includes an outer tube 120 having a plunger 121 axially movable therein, and includes a tissue-cutting linear blade 122 affixed eccentrically to the distal end of the tube 120 for puncturing an aortic wall. The plunger 121 is disposed proximal a flexible sealing disk that is rolled or otherwise compacted into the tube 120 near the distal end forward of the plunger 121. A suture attached to the sealing disk passes through the plunger for subsequent attachment to an external tensioning device of a type as previously described herein. Conventional valve-seals are disposed between the tube 120 and plunger 121, and between the plunger 121 and the sutures to permit relative movement therebetween without significant loss of blood.

In operation, the blade 122 is positioned to puncture the aortic wall and the tapered distal end of the tube 120 facilitates incursion through the puncture of the distal end into the aorta. Thus positioned, the plunger 121 is depressed relative to the tube 120 to deploy the sealing disk into the aorta from its compacted position near the distal end of the tube 120. The resilient sealing disk extends to dimensions sufficiently large to cover the puncture, with the attached tether extending through the puncture. A tensioning device such as a resilient frame 34 is then attached to the tether to exert force on the sealing disk from the external wall of the aorta to retain the sealing disk in sealing engagement with the interior aortic wall covering the puncture. An assembly of sealing disk and tether and tensioning frame may be confined within a delivery tube 123, as shown in FIG. 28m for deployment of the sealing disk within an aorta in a manner similar to the procedure as previously described herein with reference to FIGS. 4-9. Alternatively, two-part delivery apparatus may include an aortotomy punch and a separate delivery tube, as illustrated in FIG. 28l.

Each of the sealing disks illustrated in FIGS. 28a-28d may be similarly positioned as a temporary aortic sealing element, with variations in configurations associated with modifications in the surgical procedures involved in their applications. Specifically, the sealing disk of FIG. 28a includes a protruding central ridge or backbone to promote stiffness against distortion and to facilitate grasping with forceps for positioning and removal from within an aorta. The sealing disk illustrated in FIG. 28b includes a central stem as a single tether by which tension may be externally applied to retain the disk in sealing engagement with the internal wall of an aorta. The sealing disk illustrated in FIG. 28c also includes a centrally-located flexible tether and a more rigid upstanding frame to enhance positioning of the disk centrally within an aortic aperture. The sealing disk illustrated in FIG. 28d includes multiple radially-oriented corrugations between the outer upturned peripheral edge and the central elevated region at which a tether is attached. The central elevated region promotes central positioning within an aortic aperture, and the radial corrugations aid in isolating movements of the central region from disturbing the peripheral seal against the inner wall of an aorta. The upturned peripheral edge greatly facilitates formation of a good fluid-tight seal against an irregular surface of the inner wall attributable to stenotic lesions, or plaque, or the like.

Referring now to FIG. 28e, there is shown a flexible sealing disk 125 with multiple resilient tethers 127 extending therefrom to a surrounding ring of substantially rigid configuration. In this embodiment, the disk may be positioned within an aortic aperture, with the tethers 127 extending up through such aperture to their attachments to the surrounding ring that remains positioned on the outer wall of an aorta during formation of an anastomosis therewith. All of the tethers 127, except one, may then be cut and the disk 125 may be removed from the aortic aperture through an incomplete segment of the anastomosis by pulling on the remaining tether. The anastomosis may then be completed in a manner as previously described herein.

Figure 29:
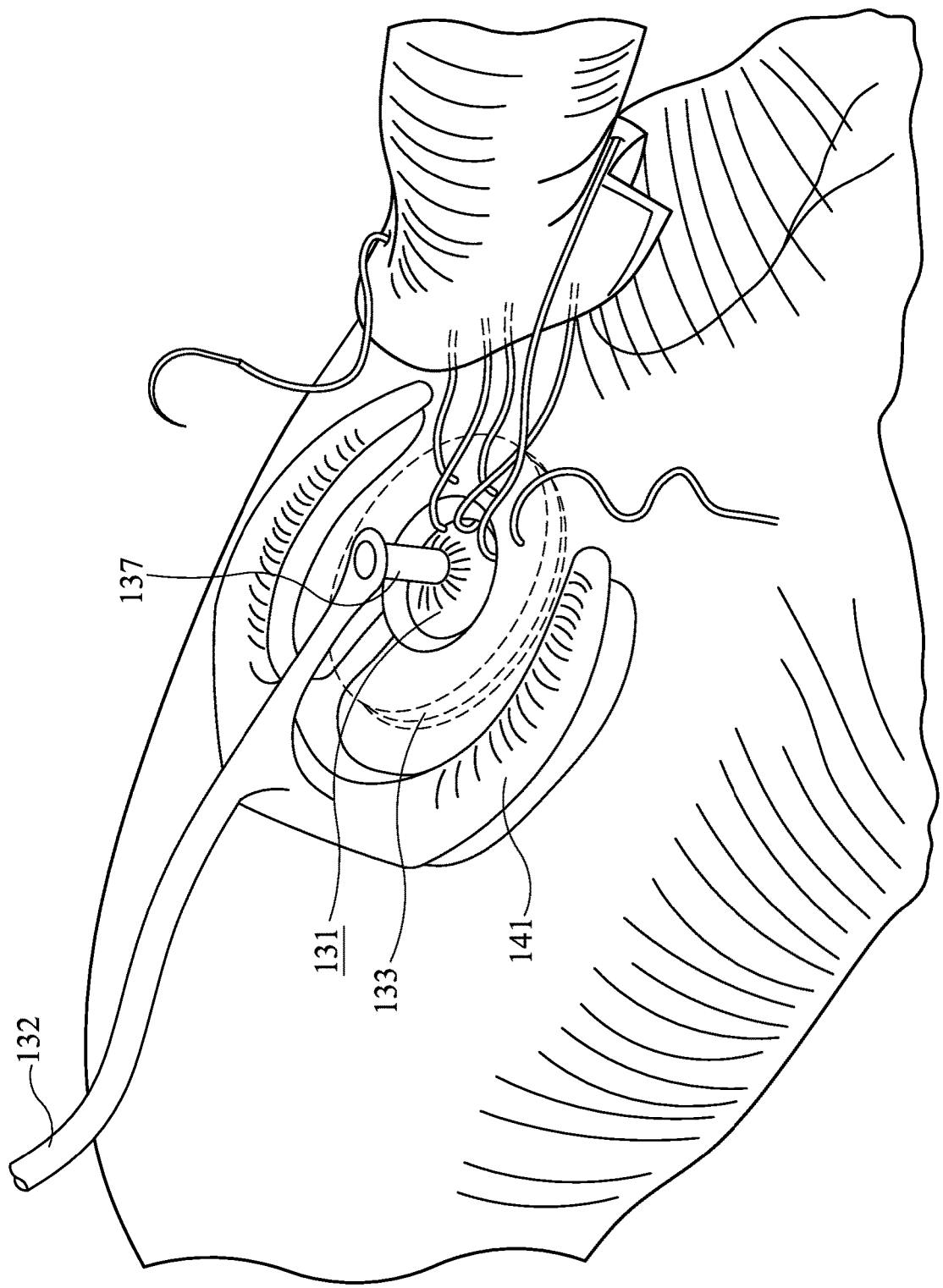
FIG. 29 is a perspective view of another embodiment of a seal according to the present invention.

Referring now to FIG. 29, there is shown a perspective view of a temporary seal in accordance with another embodiment of the present invention. The seal 131 includes an annulus-shaped balloon 133 interposed between an upper sealing member 135 and a lower support member 138, as shown in FIGS. 30a-c. The balloon 133 is connected via a lumen 132 through the central support stem 137 and frame 141 to a supply of fluid under pressure for selective inflation of the balloon 133 to form a temporary seal. As illustrated in FIG. 30a, the composite sealing element includes the upper sealing member 135 and the lower support 138, with annulus-shaped balloon 133 disposed between the upper and lower layers. All such layers and deflated balloon 133 are folded inwardly about the central stem 137 to a configuration of sufficiently small cross section to be insertable into an aortic aperture. Then, as illustrated in FIG. 30b, the balloon 133 may be inflated to exert sealing force of the upper sealing member 135 relative to the lower support member 138 and against the frame 141 disposed on the outer aortic wall. The upper sealing member 135 provides a shield for the balloon 133 against inadvertent puncture during suturing of an anastomosis, as shown in FIG. 29. Thereafter, the balloon 133 may be deflated and the sealing assembly folded inwardly and distally of the inner end of stem 137 for removal from the aorta through a partially completed anastomosis, as shown in FIG. 30c. The stitches between the aorta and graft vessel are then tightened to complete the anastomosis with negligible loss of blood.

Referring now to FIGS. 31a-d, there are shown pictorial cross-sectional views of apparatus according to the present invention for forming an aortic aperture and deploying a temporary seal to cover the aortic aperture. Specifically, an outer cylindrical sheath 151 includes a sharpened distal edge 153, and also includes a screw-like auger 155 rotatably supported therein in close-fitting engagement with the inner wall of the sheath 151. The sheath 151 also includes an auxiliary sheath 157 attached at a skewed angle to the sheath 151 for housing and selectively deploying a temporary seal 159.

Figure 31B:
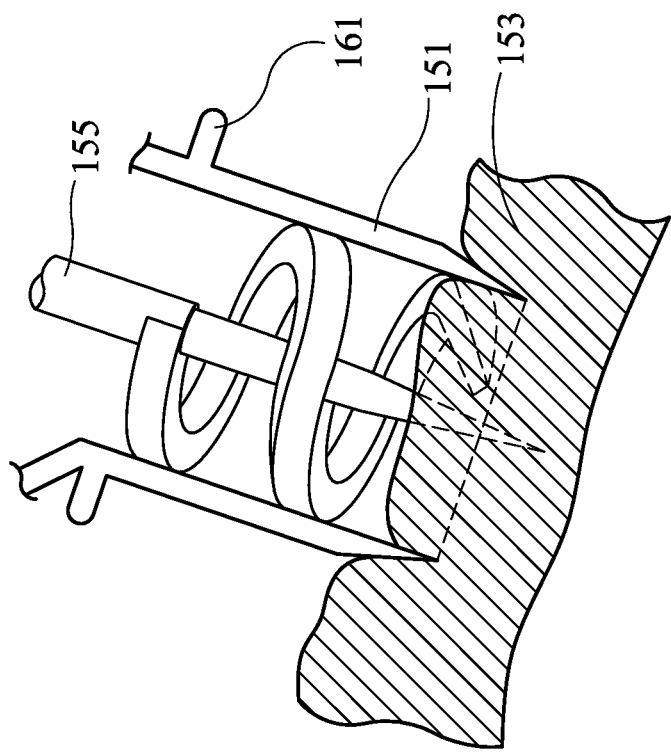
FIGS. 31a-d are sectional views of apparatus for forming and temporarily sealing an aortic aperture in preparation for formation of a proximal anastomosis.
Figure 31A:
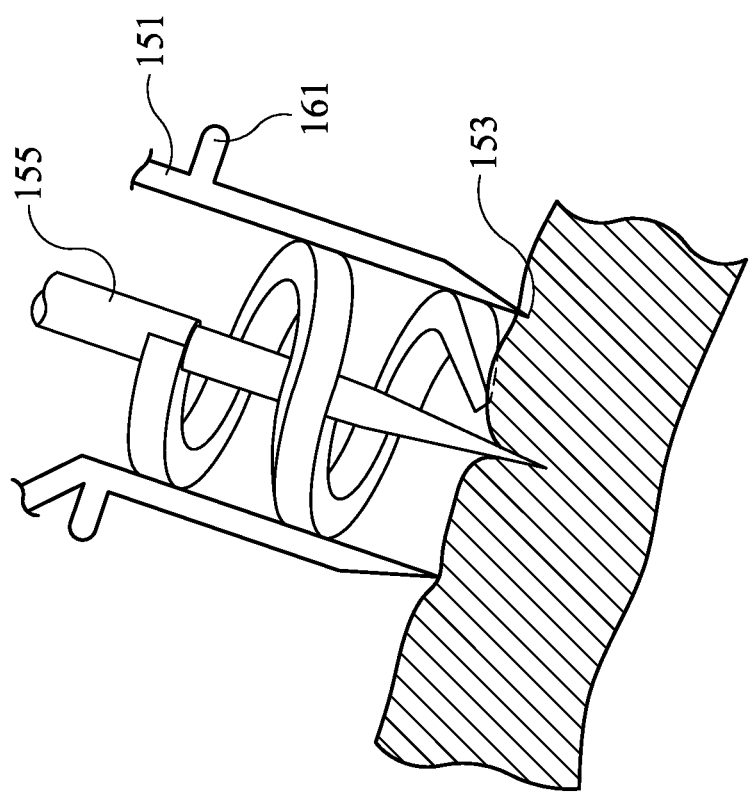
Figure 31C:
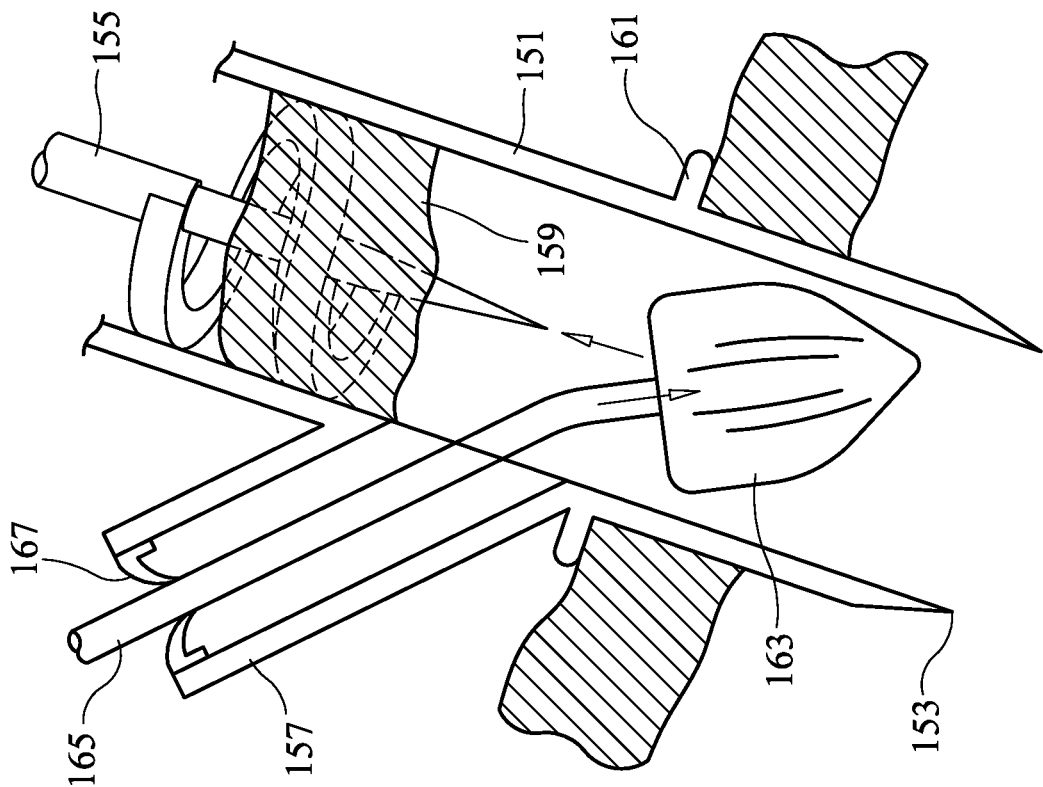
Figure 31D:
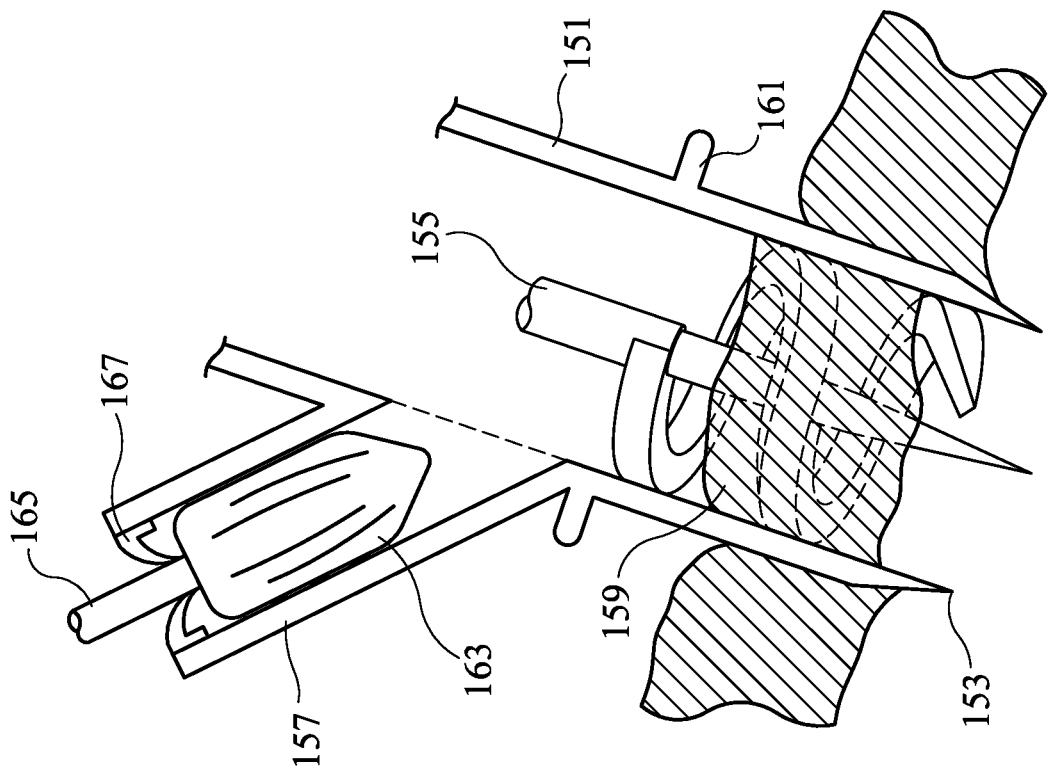

In operation, the auger 155 is rotated within the sheath 151 to auger into the wall of a vessel such as the aorta, as shown in FIGS. 31a-c. The sharpened distal edge 153 of the sheath in combination with the scissors-like shearing action of the outer edge of the auger against this sharpened distal edge 153, penetrates the aorta wall and forms a plug 159 of tissue that remains captive on the auger 155 and in substantially fluid-tight sealing engagement with the inner wall of sheath 151. The sheath is inserted into the aorta wall to a depth limited by protruding flange 161 on the outer wall of the sheath 151. As the plug 159 of tissue is withdrawn proximally within the sheath 151, an expandable seal 163 confined within the auxiliary sheath 157, as shown in FIG. 31c, is advanced into position near the distal end of the sheath 151, as shown in FIG. 31d. A flexible stem or push wire 165 is attached to the seal 163 to facilitate manual placement of the seal 163, and the stem 165 passes through a sliding seal 167 near the proximal end of the auxiliary sheath 157. Thus, the plug 159 of tissue cut from the aorta wall seals the sheath 151, and the sliding seal 167 seals the auxiliary sheath 157 as the plug 159 is withdrawn within the sheath 151 and the expandable seal 163 is inserted into the aorta through the aperture cut by the edge 153 of the sheath 151. The expandable seal 163 of a type, for example, as previously described herein resiliently expands to cover the aortic aperture as the sheath 151 is withdrawn from the aortic aperture and the sliding seal 167 passes over the length of the stem 165. An aortic aperture is thus formed and temporarily sealed with negligible loss of blood in preparation for formation of a proximal anastomosis, as previously described herein.

Figure 32A:
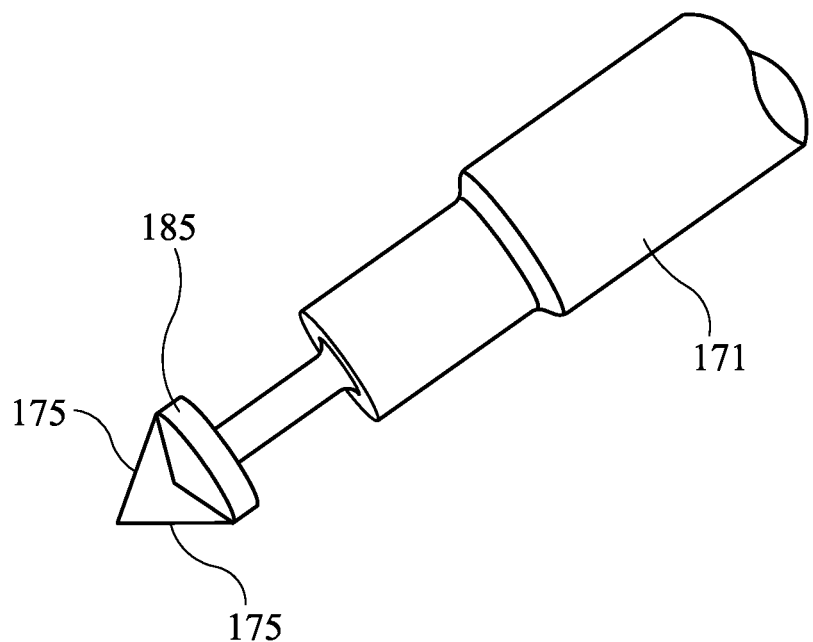
FIGS. 32a-32b are partial perspective views of an aortic punch in accordance with one embodiment of the present invention.
Figure 32B:
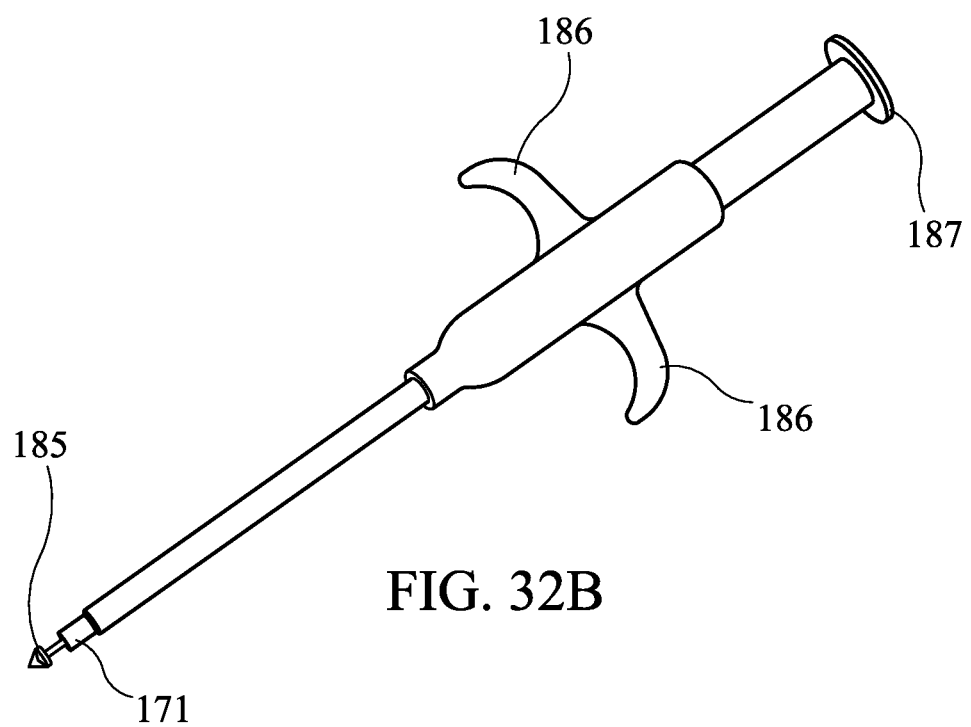

Referring now to FIG. 32a, there is a shown a partial sectional view of a punch suitable for forming an aortic aperture. Specifically, the punch 185 includes a blade with a sharpened edge 175 on the forward or distal end thereof for forming an incision as the punch 185 is inserted into the aorta. A shaft 187 of reduced cross-section relative to the punch 185 supports the punch 185 within an aortic incision with the peripheral edge of the central bore of the anvil 171 aligned with the proximal edge of the punch 185 on a syringe-type device, as shown in FIG. 32b. Manipulating the plunger 187 toward the finger grips 186 retracts the edge of the punch 185 in tissue-shearing passage through the peripheral edge of the central bore to form a well-shaped aortic aperture.

In operation, a surgeon forms a small linear incision in an aortic wall with the blade 175 as the punch 185 is inserted into the aorta. The punch is then retracted into the bore of the anvil to shear the aortic wall substantially in the shape of the punch and anvil 185, 171, with the plug of tissue to be removed captivated on the syringe-type device shown in FIG. 32b.

Figure 33A:
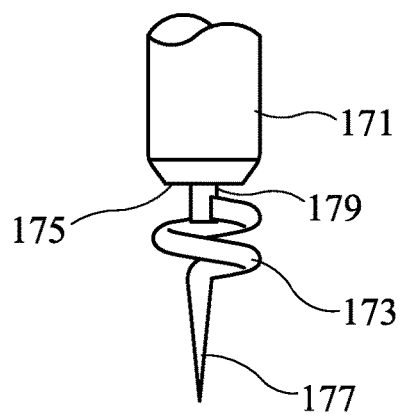
FIGS. 33a-33c are partial perspective views of an aortic punch according to an embodiment of the present invention.
Figure 33B:
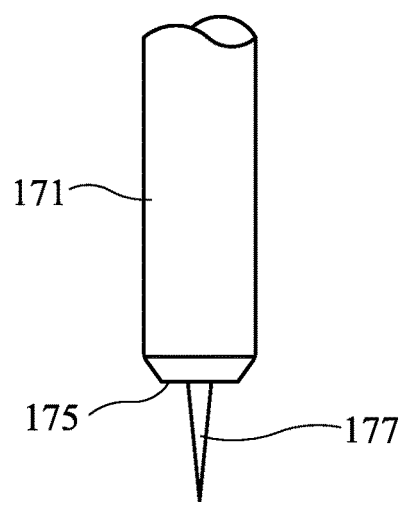
Figure 33C:
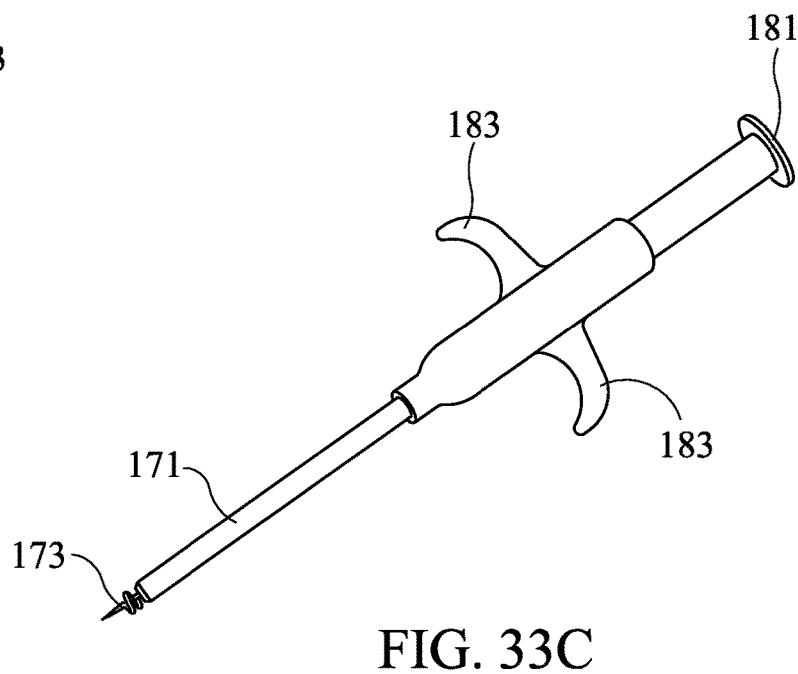

Referring now to FIGS. 33a-33c there are shown partial perspective views of an auger-like aortic punch in accordance with an embodiment of the present invention. The punch includes an outer cylindrical or elliptical anvil 171 with an internal bore that receives therein the auger 173 in translational (and optionally rotational) orientation. The lower edge of the cylindrical anvil 171 may be sharpened about the forward edge 175 of the internal bore to receive the auger 173 in close translational (and, optimally rotational) fit. A centering point 177 is attached to the distal or forward end of the auger 173 and a support shaft 179 is attached to the proximal end of the auger 173. The convolutes of the auger 173 are spaced apart and complete at least one turn about the central axis of the device. At least the trailing or proximal edge of each convolute of the auger is sharpened to promote tissue-shearing action against the sharpened edge 175 of the cylindrical anvil 171. In this way, the auger 173 may be inserted into tissue such as the aortic vessel wall with the centering point 177 initially penetrating the tissue. Then, by rotating the auger (and, optionally, the anvil 171), the convolutes of the auger penetrate the tissue through a small aperture of approximately the sectional dimension of the centering point 177 or the sectional dimension of a convolute. Thus, when used to form an aortic aperture against the pressure of blood flowing therein, resilience of the aortic wall and the small sectional dimension of the aperture thus formed therein permit negligible leakage of blood.

Then, by retracting the auger 173 into the internal bore of the anvil 171, tissue entrained on the auger 173 is drawn against the distal edge of the anvil 171, and is sheared between a sharpened proximal edge of a convolute and the distal edge of the anvil 171. In this way, a circular or elliptical aperture can be cut in the aortic wall for use, for example, in creating a coronary arterial bypass graft. The supporting shaft 179 and anvil 171 may be mounted on a syringe-style actuator, as shown in FIG. 33c, to establish relative translational motion between the anvil 171 and the auger 173 in response to the palm pad 181 being manually actuated toward finger grips 183.

Therefore, the surgical devices and procedures according to the present invention for forming a temporary aortic seal during proximal anastomosis of a graft vessel to the aorta greatly facilitate removal of the temporary seal with negligible risk of any residual debris being created thereby to circulate in blood flowing in the aorta or in the graft vessel. Additionally, sealing elements of the present invention facilitate temporarily sealing an aortotomy during formation of the vessel graft. A frame may be disposed outside the aorta to support the sealing element during formation of the anastomosis for easy removal at a convenient stage in the procedure. The sealing element thus positioned to seal off the aortotomy during formation of the anastomosis can be conveniently disassembled for removal from the surgical site with minimal additional trauma or complication of the surgical procedure.

What is claimed is:

1. An apparatus for forming a temporary fluid-tight seal on the inner wall of a fluid conduit within a patient's body, the apparatus comprising:

a fluid-impervious mushroom-shaped flange having an outer periphery and a straight, linear stem centrally formed thereon, wherein the mushroom-shaped flange has a concave surface having a radius and the stem extends within the outer periphery and beyond the radius of the concave surface, the flange including a continuous region of diminished shear strength extending from the stem along a continuous path to the periphery for selectively reconfiguring the flange in response to tension applied to the stem to disassemble the flange along the continuous region into a continuous strand, wherein the mushroom-shaped flange has a first deployed configuration and a confined configuration, wherein in the first deployed configuration the mushroom-shaped flange has a first dome configuration and in the confined configuration the mushroom-shaped flange has a configuration that is different from the first dome configuration.

2. The apparatus according to claim 1 including:
an elongated hollow sheath having an open distal end, the sheath being positioned about the stem and about the flange disposed therein in confined configuration near the distal end of the sheath.

3. The apparatus according to claim 2 including:
a plunger slidably disposed within the sheath near a proximal end thereof for selectively ejecting the fluid-impervious flange from the distal end of the sheath in response to sliding movement of the plunger within the sheath toward the distal end thereof.

4. The apparatus according to claim 2 including:
a resilient member that extends laterally and includes a pair of mating ends disposed to traverse the periphery of the flange;
a strand of flexible material attached to the mating ends and to one of the stem and flange for supporting the stem and flange intermediate the mating ends of the resilient member; and
said sheath being positioned about the flange and about the stem and the resilient member that are confined within the sheath at locations therein proximal the distal end.

5. The apparatus according to claim 4 including:
a plunger disposed within the sheath near a proximal end thereof and including a lumen therethrough;
a length of line attached to the resilient member and passing through the lumen in the plunger;
wherein the plunger is slidably disposed within the sheath to selectively eject the flange, the stem, the resilient member, and the strand of flexible material from the distal end in response to sliding movement of the plunger within the sheath toward the distal end thereof.

6. The apparatus according to claim 1, wherein the continuous region of diminished shear strength comprises a joint formed between adjacent convolutes of a wound tube or string.

7. The apparatus according to claim 1, wherein the straight, linear stem is flexible.

8. The apparatus according to claim 1, wherein the mushroom-shaped flange is configured to maintain the first dome configuration against tension applied to the stem that is less than the tension applied to the stem to disassemble the flange.

9. The apparatus according to claim 8, wherein the confined configuration constitutes a second dome configuration that is different from the first dome configuration.

10. The apparatus according to claim 9, wherein the second dome configuration is a compressed version of the first dome configuration.

11. An apparatus for forming a temporary fluid-tight seal on the inner wall of a fluid conduit within a patient's body, the apparatus comprising:
a fluid-impervious mushroom-shaped flange having an outer periphery and a straight locator thereon disposed to protrude through an aperture in a wall of the fluid conduit for positioning the flange against an inner wall over the aperture; and wherein the flange is selectively reconfigurable for removal from the aperture, the flange including a continuous region of diminished shear strength extending from the locator along a continuous path to the outer periphery for selectively reconfiguring the flange response to tension applied to the locator to disassemble the flange along the continuous region into a continuous stand, wherein the mushroom-shaped flange has a concave surface having a radius and the locator extends within the outer periphery and beyond the radius of the concave surface so as to protrude through the aperture in the wall of the fluid conduit, wherein the mushroom-shaped flange has a first deployed configuration and a confined configuration, wherein in the first deployed configuration the mushroom-shaped flange has a first dome configuration and in the confined configuration the mushroom-shaped flange has a configuration that is different from the first dome configuration.

12. The apparatus according to claim 11 in which the locator on the flange is configured to extend to a conduit outer wall beyond the aperture for providing force on the flange against the inner wall of the conduit.

13. The apparatus according to claim 11, wherein the straight locator is flexible.

14. The apparatus according to claim 11, wherein the mushroom-shaped flange is configured to maintain the first dome configuration against tension applied to the stem that is less than the tension applied to the stem to disassemble the flange.

15. The apparatus according to claim 14, wherein the confined configuration constitutes a second dome configuration that is different from the first dome configuration.

16. The apparatus according to claim 15, wherein the second dome configuration is a compressed version of the first dome configuration.

* * * * *